United States Patent [19]
Graham et al.

[11] Patent Number: 6,127,120
[45] Date of Patent: Oct. 3, 2000

[54] DETECTION OF NUCLEIC ACIDS AND NUCLEIC ACID UNITS

[75] Inventors: Duncan Graham, Edinburgh; Adrian Matthew Thornton Linacre, Glasgow, both of United Kingdom; Callum Hugh Munro, Pittsburgh, Pa.; William Ewan Smith, Glasgow, United Kingdom; Nigel Dean Watson, Ayrshire, United Kingdom; Peter Cyril White, Drymen, United Kingdom

[73] Assignee: University of Strathclyde, Glasgow, United Kingdom

[21] Appl. No.: 08/983,486

[22] PCT Filed: Jul. 25, 1996

[86] PCT No.: PCT/GB96/01830

§ 371 Date: Apr. 21, 1998

§ 102(e) Date: Apr. 21, 1998

[87] PCT Pub. No.: WO97/05280

PCT Pub. Date: Feb. 13, 1997

[30] Foreign Application Priority Data

Jul. 25, 1995 [GB] United Kingdom .................. 9517955

[51] Int. Cl.[7] .............................. C12Q 1/68; C07H 19/00; C07H 21/04; G01N 33/553
[52] U.S. Cl. ............................ 435/6; 536/22.1; 536/24.3; 536/24.31; 536/24.32; 536/25.32; 436/525; 436/164; 436/173; 436/517; 436/538; 435/91.1; 435/91.2
[58] Field of Search .......................... 435/6, 91.1, 91.2; 536/22.1, 24.3, 24.31, 24.32, 25.32; 436/525, 164, 173, 517, 538

[56] References Cited

U.S. PATENT DOCUMENTS 5,266,498  11/1993  Tarcha et al. .................... 436/525
5,306,403  4/1994  Vo-Dinh ........................ 204/182.8
5,567,628  10/1996  Tarcha et al. ...................... 436/525

OTHER PUBLICATIONS

Bertoluzza et al., J. Raman Spectroscopy, 14(6): 386–394 (1983).

Munro et al., Analyst, 120(4): 993–1003 (1995).

(List continued on next page.)

*Primary Examiner*—Jezia Riley
*Attorney, Agent, or Firm*—Dann, Dorfman, Herrell and Skillman

[57] ABSTRACT

The invention relates to the detection of target nucleic acids or nucleic acid units in a sample, by obtaining a SER(R)S spectrum for a SER(R)S-active complex containing, or derived directly from, the target. The complex includes at least a SER(R)S-active label, and optionally a target binding species containing a nucleic acid or nucleic acid unit. In this detection method, the concentration of the target present in the SER(R)S-active complex, or of the nucleic acid or unit contained in the target binding species in the SER(R)S-active complex, is no higher than $10^{-10}$ moles per liter. Additionally or alternatively, one or more of the following features may be used with the method: i) the introduction of a polyamine; ii) modification of the target, and/or of the nucleic acid or nucleic acid unit contained in the target binding species, in a manner that promotes or facilitates its chemi-sorption onto a SER(R)S-active surface; iii) inclusion of a chemi-sorptive functional group in the SER(R)S-active label. The invention also provides SER(R)S-active complexes for use in such a method, a kit for use in carrying out the method or preparing the complexes and a method for sequencing a nucleic acid which comprises the use of the detection method to detect at least one target nucleotide or sequence of nucleotides within the acid.

47 Claims, 22 Drawing Sheets

OTHER PUBLICATIONS

Kneipp et al., J. Molecular Structure, 145(1/2): 173–179 (1986).

Helmenstine et al., J. Toxicology and Environmental Health, 40: 195–202 (1993).

Cotton et al., J. Raman Spectroscopy, 22(12): 729–742 (1991).

Rubim et al., Applied Spectroscopy, 47(1): 80–84 (1993).

H. Wilson and W. E. Smith, J. Raman Spectroscopy, 25: 899–901 (1994).

T. Vo–Dinh et al., Anal. Chem., 66: 3379–3383 (1994).

J. Flemming et al., Studia Biophysica, 130(1–3): 45–50 (1989).

F. Ni et al., Anal. Chem., 62: 1958–1963 (1990).

R. Sheng et al., Anal. Chem., 63: 437–442 (1991).

K. Kneipp et al., Applied Spectroscopy, 48(3): 951–955 (1994).

AMIDE FORMATION WITH SUCCINIC ANHYDRIDE THEN EITHER
FORMATION OF ACTIVE ESTER OR COUPLING WITH AMINOHEXANOL

DETECTION OF NUCLEIC ACIDS AND NUCLEIC ACID UNITS

This is the National Stage of International Application No. PCT/GB96/01830, filed Jul. 25, 1996, which claims priority under 35 USC §119(a)–(d) to GB 9517955.2, filed Jul. 25, 1995.

FIELD OF THE INVENTION

This invention relates to methods for detecting the presence or absence of, and analysing the sequence of, target nucleic acids in a sample. Such methods may also be applied to target nucleic acid units such as nucleotides and nucleosides and their analogues. The invention also relates to chemical complexes for use in such methods, to a kit of reagents for use in carrying out the methods and to certain novel compounds of use in the methods.

BACKGROUND TO THE INVENTION
Detection of Nucleic Acids

There are many situations in which it is necessary to detect, either qualitatively or quantitatively, the presence of nucleic acids such as DNA and RNA or their constituent nucleotides. Examples of such situations include medical diagnosis (eg, the detection of infectious agents like bacteria and viruses, the diagnosis of inherited and acquired genetic diseases and the establishment of tissue type), forensic tests in criminal investigations and paternity disputes and of course the more general attempt to sequence human and animal genes.

Techniques are already known for detecting nucleic acids and nucleic acid units. Available methods include, for instance:

a) fluorescence spectroscopy—this is technically very demanding if high sensitivities are to be achieved. In biological assays, its use tends to be complicated by autofluorescence of the analytes.

b) radiolabelling—this also requires high levels of technical skill but tends to be less sensitive than fluorescence spectroscopy. It also suffers from the obvious hazards involved in handling radioactive materials.

c) chemiluminescence—although this technique can be relatively quick to carry out, and avoids the problem of autofluorescence and the need to handle toxic substances, it is unfortunately relatively insensitive and yet is still technically demanding.

A disadvantage common to many known techniques is their need for large amounts of the target analyte, ie, their relatively low sensitivity. Often in the situations mentioned above the target is simply not available in sufficiently high concentrations. As a result, the available target material has to be amplified before its presence can be accurately detected.

Again, techniques are known for amplifying a nucleic acid. The most common is the well-known "polymerase chain reaction" ("PCR"). Alternatively, the target nucleic acid may be cloned into a biological vector such as a plasmid, a phage or the like, which is then inserted into a (typically bacterial) host cell. The host is permitted to multiply and the desired vector is "harvested" from the host cell after an appropriate period of time.

Clearly, the need for amplification makes a detection method more complex, costly and time-consuming and introduces greater potential for error and for contamination of the target material.

There is therefore a need for a nucleic acid detection method which is sensitive to relatively low target concentrations, and which can preferably be carried out directly on an unamplified sample. It is this need that the present invention addresses.

Surface Enhanced Raman Scattering

The invention provides a technique based on the principle of "surface enhanced Raman scattering" (SERS) and on a modification of that principle known as SERRS (surface enhanced resonance Raman scattering). These principles are already known and well documented, and have been used before in the detection and analysis of various target materials.

Briefly, a Raman spectrum arises because light incident on an analyte is scattered due to excitation of electrons in the analyte. "Raman" scattering occurs when an excited electron returns to an energy level other than that from which it came—this results in a change in wavelength of the scattered light and gives rise to a series of spectral lines at both higher and lower frequencies than that of the incident light. The scattered light can be detected orthogonally to the incident beam.

Normal Raman lines are relatively weak and Raman spectroscopy is therefore too insensitive, relative to other available detection methods, to be of use in chemical analysis. Raman spectroscopy is also unsuccessful for fluorescent materials, for which the broad fluorescence emission bands (also detected orthogonally to the incident light) tend to swamp the weaker Raman emissions.

However, a modified form of Raman spectroscopy, based on "surface-enhanced" Raman scattering (SERS), has proved to be more sensitive and hence of more general use. The analyte whose spectrum is being recorded is closely associated with a roughened metal surface. This leads to a large increase in detection sensitivity, the effect being more marked the closer the analyte sits to the "active" surface (the optimum position is in the first molecular layer around the surface, ie, within about 20 nm of the surface).

The theory of this surface enhancement is not yet fully understood, but it is thought that the higher valence electrons of the analyte associate with pools of electrons (known as "plasmons") in pits on the metal surface. When incident light excites the analyte electrons, the effect is transferred to the plasmons, which are much larger than the electron cloud surrounding the analyte, and this acts to enhance the output signal, often by a factor of more than $10^6$. Fluorescence is also quenched, giving cleaner Raman spectra and allowing fluorescent dyes to be used as detectable analytes. Generally, the signal enhancement means that a much larger range of analytes may be usefully detected than using normal Raman spectroscopy. Furthermore, the enhancement means that a less powerful light source is required to excite the analyte molecules.

A further increase in sensitivity can be obtained by operating at the resonance frequency of the analyte (in this case usually a dye attached to the target of interest). Use of a coherent light source, tuned to the absorbance maximum of the dye, gives rise to a $10^3$–$10^5$-fold increase in sensitivity. This is termed "resonance Raman scattering" spectroscopy.

When the surface enhancement effect and the resonance effect are combined, to give "surface enhanced resonance Raman scattering" or SERRS, the resultant increase in sensitivity and robustness is more than additive. Moreover, the sensitivity does not seem to depend so critically on the angle of orientation of the analyte to the surface, as is the case with SERS alone. A SERRS signal can be more easily discriminated from contamination and background and tends to be less variable with local conditions (eg, ionic strength or pH when an analysis is carried out in solution). SERRS is thus a surprisingly sensitive detection technique; in many instances it appears to be at least as good as, if not better than, fluorescence spectroscopy (see eg, C Rodger et al, *J. Chem. Soc. Dalton Trans.* (1996), pp791–799).

SERRS can also be used selectively to detect several analytes without the need for prior separation as would be necessary for fluorescence spectroscopy (see C H Munro et al in *Analyst*, April 1995, 120, pp993–1003).

Prior Art Relating to SERS and SERRS

SERS and SERRS have been used in the past for detecting a variety of species. Examples of relevant prior art documents include:

Appl. Spectroscopy (1993), 47, pp80–84 (J C Rubim et al)—preparation of SERS-active brass surfaces and the SERS detection of benzotriazole.

J. Raman Spectroscopy (1994), 25, pp899–901 (H Wilson et al)—SERS detection of benzotriazole deposited onto a silver colloid surface.

J. Phys. Chem. (1995), 99, pp879–885 (C H Munro et al)— use of SERRS to detect an azo dye, Solvent Yellow 14, and an explanation of the mechanisms involved.

Analyst, April 1995, 120, pp993–1003 (C H Munro et al)—SERRS detection of acidic monoazo dyes.

J. Raman Spectroscopy (1991), 22, pp771–775 (J Clarkson et al)—the effects of solvent on SERS detection of organic species on silver colloid surfaces.

U.S. Pat. No. 4,674,878 (Vo-Dinh)—ways of preparing SERS substrates, and example spectra for various organic compounds (though not nucleic acids). Detection sensitivities at nanogram and sub-nanogram levels are reported.

U.S. Pat. No. 5,400,136 (Vo-Dinh)—special coatings for SERS-active surfaces. In the examples, relatively high powered lasers are used as the light source, suggesting a fairly low level of sensitivity. Again, there is no reference to nucleic acids as target analytes.

Anal. Chem. (1990), 62, p2437–2441 (J M Bello et al)—the use of fibre optic sensors in obtaining SERS spectra. Detection limits of no lower than ~$10^{-7}$ M are quoted for various organic compounds.

Appl. Spectroscopy (1995), 49, No. 6, pp780–784 (K Kneipp et al)—detection of relatively low concentration (~$10^{-16}$ M) of the dye rhodamine 6G, using SERRS. It should be borne in mind that this dye is likely to interact differently with a SERRS-active surface than would a Raman-labelled nucleic acid.

Mention has also been made of using SERS and SERRS to detect DNA and RNA. However, the concentrations detected have been relatively high. This suggests that prior art methods have not been sensitive enough to detect unamplified samples.

The following documents are relevant to the use of SER(R)S to detect nucleic acids:

J. Raman Spectroscopy (1991), 22, pp729–742 (T M Cotton et al)—this provides an overview of the applications of SERS and SERRS spectroscopy in biological systems. The detection of DNA is referred to, and potential problems are discussed. There is no indication of the detection sensitivities achievable in DNA analyses.

U.S. Pat. No. 5,306,403 (Vo-Dinh)—this proposes the detection of DNA by labelling with a dye and adsorbing the resulting complex onto a SERS-active surface. However, there is no enabling disclosure of a technique with sufficient sensitivity to be used without prior DNA amplification. Most of the examples relate to detection of isolated dyes, rather than of a dye-DNA complex (which, as explained below, would behave very differently under SERS conditions)—in these examples, the minimum dye concentration in the solutions investigated is 0.05 mg/ml, which probably equates to the detection of between ~$10^7$ and $10^{11}$ molecules. Only one example is given of the detection of a (very short) oligonucleotide labelled with aminoacridine; no concentration data is given in this example at all.

Anal. Chem. (1994), 66, pp3379–3383 (Vo-Dinh et al)—this paper reports the detection of DNA using SERS, but only at relatively high concentrations ($10^{19}$ M or greater; whilst it is impossible to make exact calculations, it is unlikely that fewer than ~$10^5$ molecules of target were detected in the examples given). These detection levels, and the reference to the use of PCR in the paper's conclusion, indicate that the technique disclosed would still be unsuitable for detecting unamplified DNA samples.

U.S. Pat. No. 5,266,498, U.S. Pat. No. 5,376,556 and U.S. Pat. No. 5,445,972 (Tarcha et al)—these describe the detection, using SERS, of an analyte by monitoring an analyte-mediated ligand binding event. A "capture reagent" is prepared by attaching a SERS-labelled binding member, specific to the target analyte, to a SERS-active surface. Binding of the specific binding member to the analyte, in a test sample, causes a detectable change in the SERS spectrum for the capture reagent. Nucleotide sequences are briefly mentioned as possible analytes, but the documents give no example of this and no explanation as to how appropriate sensitivities might be achieved, particularly for unamplified nucleotide samples.

J. Molecular Structure (1986), 145, pp173–179 (K Kneipp et al)—SERS detection of DNA on silver sols. The DNA concentration in the experiments is ~$\mu$g ml$^{-1}$; the possibility of detecting nanogram quantities of DNA is also mentioned.

Studia Biophysica (1989), 130, pp45–50 (J Flemming et al)—again, SERS detection of DNA on silver colloid surfaces, at concentrations ~$\mu$g ml$^{-1}$.

Anal. Chem. (1990), 62, pp1958–1963 (F Ni et al)—investigates the possibility of combining SERS spectroscopy with flow injection analysis, to detect RNA bases at relatively high (~$10^{-4}$ M) concentrations.

Anal. Chem. (1991), 63, pp437–442 (R Sheng et al)—use of reversed-phase high performance liquid chromatography in combination with SERS, to detect nanomolar quantities of nucleic acid bases. Sensitivity limitations are discussed, as are possible ways of overcoming them.

J. Molecular Structure (1991), 244, pp183–192 (K Kneipp et al)—SERS detection of various nucleic acids, including DNA and RNA, at concentrations no lower than ~10 $\mu$g ml$^{-1}$.

Appl. Spectroscopy (1994), 48, pp951–955 (K Kneipp et al)—near-infrared SERS detection of the DNA base adenine adsorbed onto silver or gold colloidal particles. The lowest base concentration detected is $10^{-7}$ M.

Thus, earlier experiments have in common the fact that they use relatively large quantities of nucleic acid analyte. None has yet demonstrated sensitivities high enough to allow the detection of unamplified nucleic acid samples (ie, the detection of perhaps 1–100 molecules in a sample).

That SERS and SERRS have never been proposed for use in the detection of unamplified nucleic acids is due at least in part to the obvious difficulties in achieving the appropriate sensitivities. These difficulties are partly due to problems specific to nucleic acids, problems which are therefore not addressed in the more general SER(R)S literature.

The skilled person seeking to detect nucleic acids or nucleic acid units would thus consider SER(R)S spectroscopy to lack the necessary sensitivity or robustness, certainly without target amplification. The need remains for an alternative detection method, suitable for use with very low concentrations of target, and this is what the present invention provides.

STATEMENTS OF THE INVENTION

First Aspect

According to its first aspect, the present invention provides a method for detecting the presence of a target nucleic acid or nucleic acid unit in a sample, the method comprising the steps (in any appropriate order) of:

a) forming a primary complex between a SER(R)S-active label and any target present in the sample, optionally via a target binding species containing a nucleic acid or nucleic acid unit;

b) preparing a detection sample in which the primary complex, or a secondary complex containing the label and the target binding species and derived directly from the primary complex, is associated with a SER(R)S-active surface; and c) detecting the presence of the primary or the secondary complex in the detection sample (and hence of the target in the original sample) by obtaining and analysing a SER(R)S spectrum for the detection sample;

wherein, in the detection sample, the concentration of the target present in the primary complex, or of the nucleic acid or unit contained in the target binding species in the secondary complex, is no higher than $10^{-10}$ moles per liter.

The target, the label, the primary target-label complex, the target binding species, the secondary complex and the SER(R)S-active surface are more specifically defined below. Concentration in the detection sample refer to concentrations in the sample actually under investigation, ie, in the case of a fluid phase investigation, the sample from which a SER(R)S spectrum is directly taken or, in the case of a solid phase investigation, the sample which is applied to a SER(R)S-active surface in order to obtain a spectrum.

Clearly, subject to practical constraints, there is no lower limit on the nucleic acid/nucleic acid unit concentration which the present invention may be used to detect. For instance, it might usefully be carried out using detection samples containing fewer than 100 copies, for example fewer than 50, or perhaps fewer than 20 or fewer than 10 copies or, in particular, fewer than 5 copies of the relevant nucleic acid or nucleic acid unit. Certainly the detection of picomolar ($10^{-10}$ to $10^{-12}$ moles per liter) or femtomolar ($10^{-13}$ to $10^{-15}$ moles per liter) or lower, possibly much lower, perhaps attomolar ($10^{-16}$ to $10^{-18}$ moles per liter) concentrations, or even below, can be envisaged.

The method may of course also be used to establish the absence of the target in the sample, by carrying out the same steps and detecting an absence of the relevant primary or secondary complex in the detection sample.

As explained above, neither SERS nor SERRS has been used in the past to detect nucleic acids at such low concentrations, ie, at concentrations likely to represent unamplified samples of target material. The present invention makes such detection possible by greatly increasing the sensitivity of conventional SER(R)S techniques, hence providing a completely new and improved method for detecting nucleic acids and their constituent units, a method which can potentially be carried out much more quickly and cheaply, and with less skill, than existing detection methods.

The increased sensitivity may be achieved, in the present invention, in the manner described below. It involves the use of at least one, preferably more, of three modifying features, all of which help to bring the primary or secondary complex into closer proximity with the SER(R)S-active surface being used to obtain the SER(R)S spectrum.

Second Aspect

Thus, a preferred, second, aspect of the invention provides a method for detecting the presence or absence of a target nucleic acid or nucleic acid unit in a sample, the method comprising the steps (in any appropriate order) of:

a) forming a primary complex between a SER(R)S-active label and any target present in the sample, optionally via a target binding species containing a nucleic acid or nucleic acid unit;

b) preparing a detection sample in which the primary complex, or a secondary complex containing the label and the target binding species and derived directly from the primary complex, is associated with a SER(R)S-active surface; and c) detecting the presence or absence of the primary or the secondary complex in the detection sample (and hence of the target in the original sample) by obtaining and analysing a SER(R)S spectrum for the detection sample;

wherein one or more of the following features is used:

i) the introduction into the detection sample, prior to detection, of a monomeric or polymeric polyamine;

ii) modification, prior to detection, of the target, and/or of the nucleic acid or nucleic acid unit contained in the target binding species, in a manner that promotes or facilitates its chemi-sorption onto the SER(R)S-active surface;

iii) inclusion of a chemi-sorptive functional group in the SER(R)S-active label.

For this method too, the concentration in the detection sample of the target present in the primary complex, or of the nucleic acid or unit contained in the target binding species in the secondary complex, is preferably no higher than $10^{-10}$ moles per liter.

This method makes use of at least one (preferably more than one, more preferably all three) modification to enhance the sensitivity of existing SER(R)S detection methods, thus allowing it to be used, in some cases, to detect extremely low concentrations of unamplified target.

The effect of each of features (i)–(iii) in increasing sensitivity is believed to be at least additive; two or more features used together can have a synergistic effect on detection sensitivity. Each feature is described in more depth below, following the explanation of terms used in defining the invention.

Meaning of SER(R)S

Firstly, by SER(R)S is meant either surface enhanced Raman scattering or surface enhanced resonance Raman scattering. The methods of the invention may involve either form of spectroscopy, since the essential principle (the association of a Raman-active label with a Raman-active surface) is the same in each case. Preferably, the methods of the invention involve SERRS rather than SERS, since operating at the resonant frequency of the label gives increased sensitivity—in this case, the light source used to generate the Raman spectrum is a coherent light source (eg, a laser) tuned substantially to the maximum absorption frequency of the label being used. (Note that this frequency may shift slightly on association of the label with the SER(R)S-active surface and the target and/or target binding species, but the skilled person will be well able to tune the light source to accommodate this. Note too that the light source may be tuned to a frequency near to the label's absorption maximum, or to a frequency at or near that of a secondary peak in the label's absorption spectrum.)

SERRS may alternatively involve operating at the resonant frequency of the plasmons on the active surface, although in the methods of the invention it is believed to be preferable to tune to the resonant frequency of the label.

Type of Target and Sample

The methods of the invention may be used for the quantitative or qualitative detection of target nucleic acids and nucleic acid units, and to detect the absence as well as the presence of a target in a sample. They may form part of an overall method for determining the sequence of a nucleic acid, by detecting the presence in it of several selected target nucleotides or nucleotide sequences.

The target nucleic acid may be a naturally occurring DNA, RNA, mRNA, rRNA or cDNA, or a synthetic DNA, RNA, PNA or other nucleic acid analogue. Typically, it will be a naturally occurring DNA or RNA. It may be an oligonucleotide or a polynucleotide. In this document, unless the context requires otherwise, the term "nucleotide" is used to refer to either a deoxyribo- or a ribo-nucleotide or an analogue thereof; "oligonucleotide" to a nucleotide sequence of between 2 and 100 base units; and "polynucleotide" to a nucleotide sequence of 50 base units or more.

Target oligonucleotide or polynucleotide may be substantially single- or double-stranded. It will be appreciated that an initial target may be subjected, prior to detection, to molecular biological manipulations such as digestion with restriction enzymes or copying by means of nucleic acid polymerases, thus allowing modifications to be introduced into it.

The target may be a nucleic acid "unit", by which is meant a nucleotide or nucleoside or a modified nucleotide or nucleoside or a nucleotide or nucleoside analogue, or an individual nucleobase. The choice of target will depend on the purpose for which the detection method is ultimately to be used—eg, for detecting the presence of bacteria or viruses in cells, it is likely that genomic DNA or RNA would be the most suitable target to detect.

The sample may be any suitable preparation in which the target is likely to be found. In the case of medical diagnostic techniques, for instance, the sample may comprise blood (including plasma and platelet fractions), spinal fluid, mucus, sputum, semen, stool or urine. Particularly suitable samples include, eg, 20–1000 $\mu l$ of blood or 1–10 ml of mouthwash. Samples may also comprise foodstuffs and beverages, water suspected of contamination, etc . . . These lists are clearly not exhaustive.

The sample will typically be pre-treated to isolate the target and make it suitable for subsequent SER(R)S analysis. Many methods and kits are available for pre-treating samples of various types.

The detection sample may be in any appropriate form such as a solid, a solution or suspension or a gas, suitably prepared to enable recordal of its SER(R)S spectrum. The detection sample can be at any suitable pH, typically an acidic pH.

The SER(R)S-Active Label

The label can be any suitable material which is SER(R)S-active, ie, which is capable of generating a SERS or SERRS spectrum when appropriately illuminated. It must also be capable of forming a primary complex with the target, either directly or via a target binding species, in the manner described below.

It is possible in some cases, particularly when using SERS spectroscopy, that the target itself, or the target binding species, could also act as the SER(R)S-active label, capable of generating its own Raman spectrum.

Many SER(R)S-active labels are already known and referred to in SER(R)S literature. They include species containing chromophores and/or fluorophores which can be detected relatively easily using SER(R)S.

Examples of suitable SER(R)S-active species include fluorescein dyes, such as 5- (and 6-) carboxy-4',5'-dichloro-2',7'-dimethoxy fluorescein, 5-carboxy-2',4',5',7'-tetrachlorofluorescein and 5-carboxyfluorescein; rhodamine dyes such as 5- (and 6-) carboxy rhodamine, 6-carboxytetramethyl rhodamine and 6-carboxyrhodamine X; phthalocyanines such as methyl, nitrosyl, sulphonyl and amino phthalocyanines; azo dyes such as those listed in C H Munro et al, *Analyst* (1995), 120, p993; azomethines; cyanines and xanthines such as the methyl, nitro, sulphano and amino derivatives; and succinylfluoresceins. Each of these may be substituted in any conventional manner, giving rise to a large number of useful labels. The choice of label in any given case will depend on factors such as the resonance frequency of the label, the other species present, label availability, etc . . .

Most preferred are labels containing a chemi-adsorptive functional group, described below in connection with feature (iii) of the invention.

Preferred SER(R)S-active labels are, moreover, those which possess appropriate functional groups to allow their easy attachment both to the target (or an appropriate target binding species) and to the SER(R)S-active surface. The label should clearly not contain groups likely to interfere with the target or the target binding species.

Where the label is to be bound to the target via a target binding species, the label is preferably used in the form of a pre-prepared label-binding species complex. Ways in which labels may be complexed with target binding species are outlined below.

The Target Binding Species

Typically when carrying out the methods of the invention, it will be necessary to bind the target to the SER(R)S-active label via a target binding species. This may be in the form of, or contain, a nucleic acid or nucleic acid unit which is substantially complementary to at least part of the target—in other words, the target binding species is typically a form of nucleic acid probe or primer specific to the target. (By "substantially complementary" is meant that the nucleic acid or unit is capable of selective hybridisation to the target.) Subsequent detection of the SER(R)S-active label attached to the target binding species gives information as to the presence (or absence) of any target to which it is, or has been, bound.

The Primary Target-Label Complex

The primary complex, as described above, generally involves the specific binding of at least a part of the target with a target binding species which is in turn attached to the SER(R)S-active label. The main requirement of the target-label link is that it forms a complex of the two species so that detection of the label by means of its SER(R)S spectrum would be equivalent, in effect, to detection of the attached target.

The link between the label and the target, or where applicable between the label and the target binding species, may involve any suitable form of attachment. Many methods are known, eg, from fluorescence spectroscopy, for linking dyes and other labels to nucleic acids and/or nucleic acid units. Some involve chemical modification of the basic label structure. The skilled person would have no difficulty in selecting one appropriate for the particular label, target and target binding species concerned. The attachment may be direct, via a covalent bond or chelating link, for instance. More preferably it is indirect through a separate linking group—again, appropriate linking groups are known, and these can help separate the label from attached nucleic acids and nucleic acid units which can potentially (as explained below) interfere with the vital interaction between the label and the SER(R)S-active surface. DNA binding proteins may, for instance, function as "linking groups" in this context.

The label is preferably attached to the 5' end of the relevant nucleic acid or nucleic acid unit, although attachment to the 3' end or to an intermediate position (eg, to a base or to a backbone sugar group) is also possible.

Two methods by which a SER(R)S-active label may be attached to a nucleic acid or nucleic acid unit include, for instance:

1. The nucleic acid (or unit) is synthesised with a nucleophilic primary amino group, usually at the 5'-terminus. After deprotection it is reacted with an appropriate reactive site (eg, an active ester site) on the label. Purification, usually by chromatography, yields the desired product. (See eg, J Goodchild, *Bioconjugate Chem.* (1990), 1, pp165–187.)

2. The label is synthesised with a chemical group (usually an alcohol) capable of undergoing phosphorous functionalisation. The active phosphorous compound is then reacted with the nucleic acid or nucleic acid unit. This reaction can be accomplished using several types of standard chemistry, as detailed for example in M J Gait, *Oligonucleotide Synthesis: A Practical Approach* (1984), IRL Press Oxford.

Further examples of suitable attachments, including via linking groups, appear in P Theisen et al, *Tetrahedron Letters* (1992), 33, No. 35, pp5033–5036; J M Prober et al, *Science* (1987), 233, pp336–341; D B Shealy et al, *Anal. Chem.* (1995), 67, pp247–251; and C Mackellar et al, *Nuc. Acids Res.* (1992), 20, pp3411–3417.

Still further examples of ways in which a SER(R)S-active label may be bound to a nucleic acid or nucleic acid unit are the following typical known methods. Although 5' labelling of nucleic acids is illustrated, essentially identical modifications of the 3' end and/or of internal sites are equally feasible.

Modified Dye

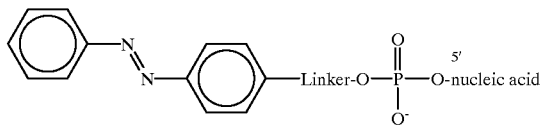

(See P Theisen et al, supra.)

Coupled Dye (Coupling May Take Place in Situ)

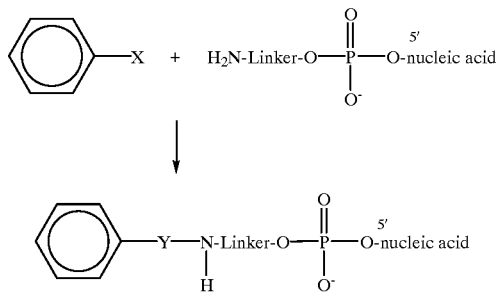

(X=a suitable group for attack by a primary amine, eg, isothiocyanate or N-succinamide; Y is its derivatised form.)

(See J Goodchild, supra for a specific example.)

Coupled Dye With a Modified Nucleobase

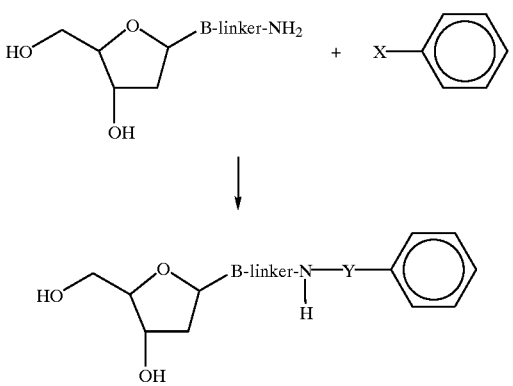

(X, Y=as above; B=any base in the nucleic acid or nucleic acid unit. Where the nucleic acid or unit is a target binding species, the product may then be used as a monomer in the synthesis of a labelled polynucleotide suitable for binding to the target being detected.)

(See J M Prober et al, supra.)

The Secondary Complex

The "secondary complex" is derived directly from the primary target-label complex, so that its presence depends on the formation of the primary complex. Detection of the secondary complex, even if the original target is no longer present, then corresponds (both qualitatively and preferably quantitatively) to detection of the target. The secondary complex still contains the SER(R)S-active label, so as to yield a detectable SER(R)S spectrum.

A secondary complex may be formed, for instance, by cleaving away all or part of the original target from the primary target-label complex. There are other similar situations in which a secondary complex may be derived directly from the primary one by the addition or removal of species—the only requirement is that the presence of the secondary complex in the detection sample reflects the presence of the primary complex in the original sample.

At the time of detection, the primary and secondary "complexes" need not involve direct links, such as covalent bonds, between their constituent species. Also envisaged are situations in which, for instance, the target or the target binding species is merely associated with the label, ie, it is still present in the detection sample and its presence is still capable of influencing the interaction of the other species present and therefore the SER(R)S spectrum, but it has for example been cleaved from the label-containing complex.

Order of Combination of Species

The order of combination of the target, the label (with target binding species if used) and the SER(R)S-active surface is not critical in the methods of the invention.

Preferably the primary or secondary complex is formed and then added to the active surface. As an alternative, the first step may be to confirm the presence (or absence) of the target by reaction with a target binding species, which can subsequently be detected by the addition of an appropriate SER(R)S-active label and surface.

It is also possible to envisage a situation in which the target is brought into contact with an appropriate surface (eg, in the form of a coating on a waveguide) prior to addition of the label and target binding species if necessary.

In each case, the result should be a system in which the label-containing complex is associated with, and ideally sits as close as possible to, the electron pools on the active surface. Features (i)–(iii), described below, all help to optimise the proximity between the complex and the surface, thus increasing sensitivity.

The SER(R)S-Active Surface

The SER(R)S-active surface may again be any suitable surface, usually metallic, which gives rise to enhancement of the Raman effect, of which many are known from the SER(R)S literature. It may for instance be an etched or otherwise roughened metallic surface, a metal sol or, more preferably, an aggregation of metal colloid particles. Silver, gold or copper surfaces, especially silver, are particularly preferred for use in the present invention and again, aggregated colloid surfaces are believed to provide the best SER(R)S effect.

The surface may be a naked metal or may comprise a metal oxide layer on a metal surface. It may include an organic coating such as of citrate or of a suitable polymer, such as polylysine or polyphenol, to increase its sorptive capacity.

Where the surface is colloidal, the colloid particles are preferably aggregated in a controlled manner so as to be of a uniform and desired size and shape and as stable as possible against self-aggregation. Processes for preparing such unaggregated colloids are already known. They involve, for instance, the reduction of a metal salt (eg, silver nitrate) with a reducing agent such as citrate, to form a stable microcrystalline suspension (see P C Lee & D Meisel, $J.$ $Phys.$ $Chem.$ (1982), 86, p3391). This "stock" suspension is then aggregated immediately prior to use. Suitable aggregating agents include acids (eg, $HNO_3$ or ascorbic acid), polyamines (eg, polylysine, spermine, spermidine, 1,4-diaminopiperazine, diethylenetriamine, N-(2-aminoethyl)-1, 3-propanediamine, triethylenetetramine and tetraethylenepentamine) and inorganic activating ions such as $Cl^-$, $I^-$, $Na^+$ or $Mg^{2+}$. To increase control over the process, all equipment used should be scrupulously clean, and reagents should be of a high grade. Since the aggregated colloids are relatively unstable to precipitation, they are ideally formed in situ in the detection sample and the SER(R)S spectrum obtained shortly afterwards (preferably within about 15 minutes of aggregation).

Ideally, a material such as spermine or spermidine is introduced to assist control of the aggregation process—see the discussion of feature (i) below. The aggregation may be carried out at the same time as, or shortly after, the surface is introduced to the other species in the detection sample.

The colloid particles are preferably monodisperse in nature and can be of any size so long as they give rise to a SER(R)S effect—generally they will be about 4–50 nm in diameter, preferably 25–36 nm, though this will depend on the type of metal.

Preferably, the surface comprises silver colloid particles, which are preferably substantially hexagonal in shape and of about 20–36 nm maximum diameter.

Association of the Label-Containing Complex With the Surface

The "association" of the label-containing complex (ie, the primary or the secondary complex) with the SER(R)S-active surface will typically be by chemi-sorption of the complex onto the surface, or by chemical bonding (covalent, chelating, etc.) of the complex with a coating on the surface, either directly or through a linking group. The association will usually be via suitable functional groups on the label, such as charged polar groups (eg, $NH_3^+$ or $CO_2^-$), attracted to the surface or surface coating (eg, to free amine groups in a polyamine coating). Clearly, the type of association will depend on the nature of the surface and the label in any given case; different functional groups will be attracted to a positively-charged surface, for instance, as to a negatively-charged one.

Suitable groups by which the complex may be bound to the active surface include complexing groups such as nitrogen, oxygen, sulphur and phosphorous donors; chelating groups; bridging ligands and polymer forming ligands—examples of these include:

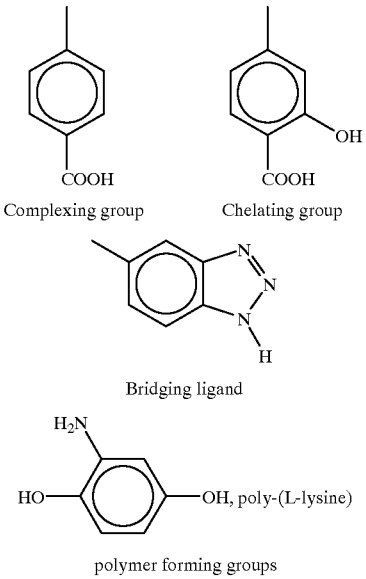

Preferred ways of optimizing the attachment between surface and label-containing complex are described in connection with features (i)–(iii) below.

Features (i)–(iii)

Turning now to features (i)–(iii) of the methods of the invention, all three of these are designed to increase the sensitivity of the methods, by facilitating the best possible contact between the SER(R)S-active surface and the label-containing complex. Each feature helps to achieve this in a slightly different way, and some offer further advantages as well.

Identification of these features, and of their effects on sensitivity, has led to a greater understanding of the problems of applying SER(R)S to nucleic acids and nucleic acid units, and of the lack of sensitivity previously encountered. In order to achieve sensitive SER(R)S detection, the SER (R)S-active label must be able to approach the SER(R)S-active surface at least to within about 20 nm, ie, to within the first molecular layer. Generally, the closer the approach the better; Raman signal enhancement is proportional to $1/r^2$ where r is the distance between the surface and the label. When the label is attached to a nucleic acid target or target binding species, of a size typically of use in molecular biology (at least 8 bases in length), two factors inhibit label-surface proximity and hence detection sensitivity: (a) the nucleic acid is far larger than the label which interferes sterically with the label-surface interaction; and (b) the nucleic acid is a polyanion carrying a negative charge on each nucleotide residue; it is therefore electrostatically repelled by negatively-charged species such as the reducing agents which tend to be associated with typically-used SER(R)S-active surface (in particular, colloids), and this again interferes with the approach of the label to the surface.

Thus, to bring the label into sufficient proximity with the surface, it is firstly necessary to bring the attached nucleic acid closer to the surface than would normally be possible.

Features (i)–(iii) seem to be effective in overcoming these hurdles and facilitating a better label-surface interaction. Feature (i) is particularly preferred for use in the methods of the invention, although ideally it is combined with one or more of features (ii) and (iii).

To take each feature in turn:

(i) Introduction of Polyamine

Firstly, by "polyamine" is meant an amine having more than one amino group per molecule. The term includes both monomeric and polymeric polyamines; in the case of polymeric polyamines, there must be more than one amino group per monomer or per repeat unit of the polymer.

The introduction of a polyamine has been found greatly to enhance the sensitivity of the methods of the invention. This is thought to be at least partly due to the ability of the polyamine to "balance" some of the net negative charge associated with the target nucleic acid or nucleic acid unit (and/or with any target binding species used); an "ion pair" seems to be formed between the polyamine and the nucleic acid (unit). The polyamine also seems to act as a large positively charged ligand (containing as it does a relatively high concentration of free amino groups) on the SER(R)S-active surface, which seems to enable the primary or secondary complex more easily to approach, and better to adhere to, the surface. This in turn increases sensitivity and robustness.

Surprisingly, some polyamines have been found to give a further advantage when the surface is a metal colloid; they assist in controlling colloid aggregation, allowing it to proceed in a more controlled fashion to produce a more uniform and time stable product. Again, this may well be due to the ability of the polyamine to reduce the charge on the metal particles, necessary for efficient aggregation to occur. Spermine and spermidine, especially spermine, have a particularly good effect on colloid aggregation and so are highly preferred for use in the present invention.

When high levels of sensitivity are needed, as is the case for nucleic acid targets, the quality of the active surface becomes more important than in many prior art techniques—for a colloidal surface, for instance, the aggregated colloid particles should be of an optimum (and uniform) size and shape. The use of a polyamine such as sperm(id)ine assists in achieving this.

The prior art describes the use of polylysine (a polymeric amine containing only one amino group per repeat unit) as a coating for a SER(R)S-active surface, to modify the charge on anionic SER(R)S-active dyes (see eg, C H Munro et al in *J. Phys. Chem*, supra). However, polylysine does not promote the nucleic acid-label-surface interaction in the way that polyamines do according to the present invention; in particular it is unable to modify a nucleic acid charge in the same way. The prior art fails to recognise that polyamines, such as spermine or spermidine, might be useful both to assist in colloid formation and to increase the affinity of the active surface for the label-containing complex. The discovery that they can do this is both new and unexpected.

Because of the dual function of the polyamine, it is preferably introduced, in the detection sample, to a precursor to a colloidal SER(R)S-active surface (eg, the microcrystalline solution described above); the polyamine then both promotes aggregation of the colloid, and at the same time modifies the negative charge on nucleic acids or nucleic acid units present. Excess polyamine remains as a coating on the surface, which the label-containing complex can more easily approach and bind to.

In more general terms, the polyamine should be introduced at a time which allows its interaction with the target and/or the target binding species, before the SER(R)S spectrum is obtained. For instance, it may be added to the label-binding species complex, prior to introducing the label and binding species into the sample containing the target material. Alternatively it may be added to the target sample prior to introducing the label (and optionally the binding species) and later the SER(R)S-active surface. Once the surface is combined with the other reagents, the result is a "chain" of association from the surface, through any coating which may be present on it, through its further polyamine coating, to the label-containing complex to be detected.

The polyamine is preferably a short-chain aliphatic polyamine such as spermine, spermidine, 1,4-diaminopiperazine, diethylenetriamine, N-(2-aminoethyl)-1,3-propanediamine, triethylenetetramine and tetraethylenepentamine (see structural formulae below); spermine and spermidine, in particular spermine with its four $NH_2$ groups per repeat unit, are most preferred for use in the present invention. The polyamine is preferably introduced in the form of an acid salt such as its hydrochloride. As described above, it is of most use when the SER(R)S-active surface is colloidal.

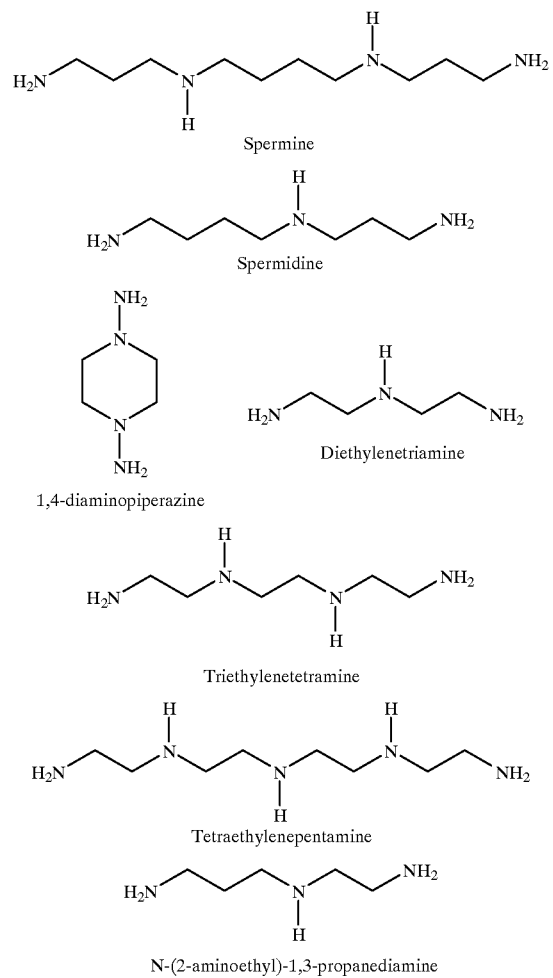

The amount of polyamine added is preferably of the order of 100 to 1000 times more than would be needed to obtain a monolayer coverage of the surface with the polyamine. In the case of a colloidal surface, this can be calculated with reference to the size of the colloid particles.

(ii) Modification of the Target or Target Binding Species

Again, modifying the target or target binding species (itself containing a nucleic acid or nucleic acid unit), to promote or facilitate its chemi-sorption onto the SER(R)S-active surface, can help stabilise the interaction between the label-containing complex and the surface, and increase the sensitivity and robustness of the methods of the invention.

The modification may facilitate the chemi-sorption at least in part by reducing the overall negative charge of the nucleic acid or nucleic acid unit. Ideally, the modification is such as to achieve both effects, ie, promotion or facilitation of chemi-sorption and a reduction in net negative charge.

Modification may be achieved in a number of ways, of which the most preferred are either to incorporate one or more appropriate functional groups into the nucleic acid (unit), or to make use of a neutral analogue (see description below). The two modifications may be combined if desired to give a greater overall effect, although care should be taken not to over-modify to the extent that the nucleic acid (unit) fails to hybridise effectively in the manner required of it. Preferably, modification is combined in the methods of the invention with the use of a polyamine according to feature (i). It is conveniently carried out on a target binding species such as a nucleic acid probe or primer.

Incorporation of functional groups

Suitable functional groups include the Lewis bases, such as thiols and amines which can easily be added to nucleic acids. A most preferred functional group is one which can provide additional cationic sites (under the test conditions used), eg, one comprising an amino, preferably a primary amino, group or groups. Amino groups can be attached to a nucleic acid (unit) via a spacer arm at various positions including the 5' and 3' terminal hydroxy groups, as is well known in the art. They can also be attached to nucleobases, especially the C5 position of thymidine or uridine, as is also known.

Specific examples of 5' and 3' amino modifiers which can be attached to a nucleic acid (unit) include alkylamino groups $H_2N-(CH_2)_n-$ where n is any integer greater than 1, and amino-ethyleneglycols $H_2N-(CH_2CH_2O)_n-$ where n is any integer greater than 1. Specific examples of thymidine or uridine modifiers, for instance, are $-CH=CH-CO-NH-(CH_2)_n-NH_2$ and $-CH=CH-CO-NH-(CH_2CH_2O)_n-CH_2CH_2NH_2$, again with n being any integer greater than 1.

A further example of an amino-modified thymidine if 5-(3-aminoprop-1-yn-1-yl)-2'-deoxyuridine:

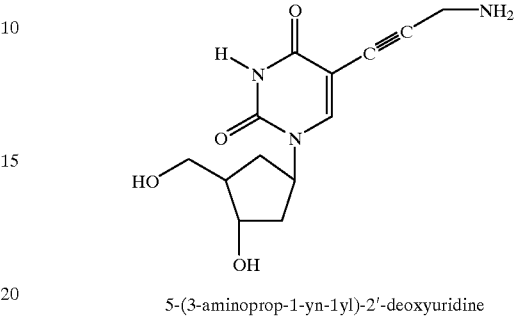

5-(3-aminoprop-1-yn-1yl)-2'-deoxyuridine (see K A Cruickshank et al, *Tetrahedron Letts.* (1988), 29, pp5521–5224 for synthesis).

A further useful amino modification would be to prepare a polyaminolinker from the C5 position of thymidine or uridine or from any other suitable position on a nucleic acid (unit). This could be achieved, for example, in one step starting from the known compound 5-(3-acrylyl)thymidine, reacting with a polyamine such as spermine to form an amide bond using a peptide coupling agent such as dicyclohexylcarbodiamide (DCC):

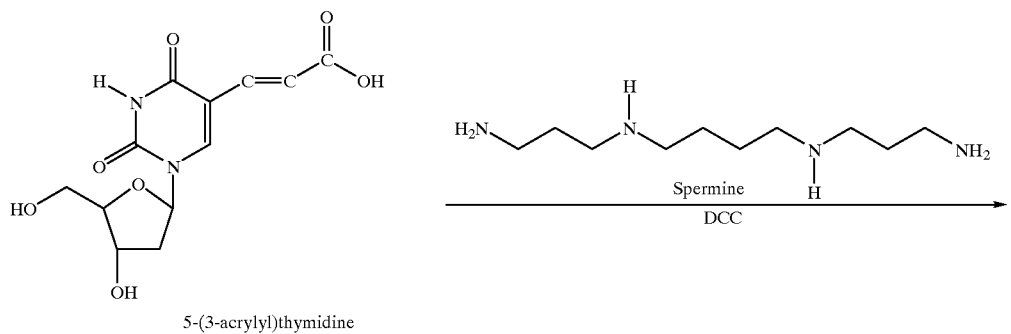

5-(3-acrylyl)thymidine

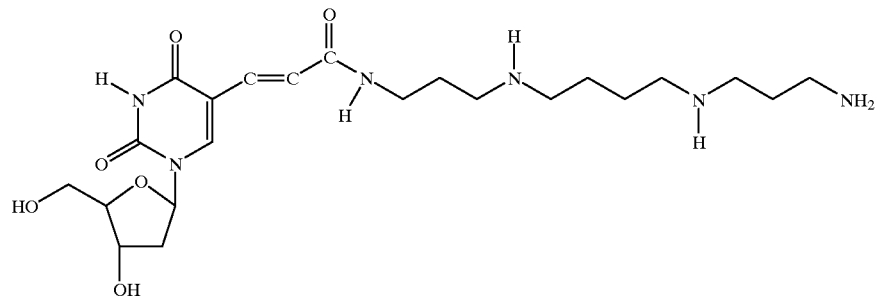

Modification conveniently takes place at the bases of the nucleic acid (unit). It may occur at more than one position, the degree of modification possible being dependent on chemical and stereochemical possibilities. Within reason, a greater level of modification generally gives a greater detection sensitivity in the methods of the invention.

Neutral analogues

Neutral analogues of nucleic acids, in which one or more (or even all) of the internucleotide phosphodiester linkages are replaced with an electrically neutral moiety, are well known in the art and are also of use in the present invention, in particular as target binding species.

In wild-type nucleic acids the backbone has a repeat of six atoms between residues which consist of the 3' carbon of one (deoxy)ribose sugar ring, the 4' and 5' carbons of the same (deoxy)ribose residue, the oxygen attached to the 5' carbon, the phosphorous attached to this oxygen and the oxygen joined both to the phosphorous and to the 3' carbon of the following (deoxy)ribose ring in the 5' direction. In neutral nucleic acid analogues this inter-residue six atom repeat motif is usually maintained. Most commonly the use of (deoxy)ribose sugar rings is retained and therefore two of the atoms usually consist of the 3' and 4' carbons of (deoxy)ribose rings but each, all of any combination of the remaining four atoms of the linkage may be replaced with other atoms or functional groups. Some examples of these electrically neutral internucleotide linkages are shown in Table 1 below.

Several other neutral nucleic acid analogues are known where the (deoxy)ribose rings of the backbone as well as the inter-ring atoms are replaced by other atoms or functional groups. These include but are not restricted to peptide nucleic acids (PNA), ornithine peptide nucleic acids are morpholine carbamates (see structural formulae below Table 1).

Table 1

(In the following formulae, B represents any nucleobase and R represents any appropriate functional group, including hydrogen, of which examples will be well known to the skilled person.)

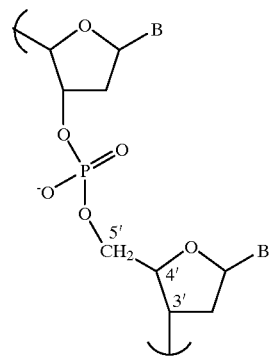

Inter-residue C3'—C4'—C5'—O—P—O linkage of nucleic acids.

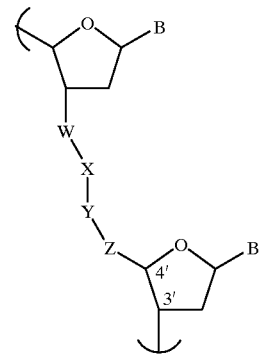

Replacement of the C5'—O—P—O motif with other atoms or functional groups with retention of the C3' and C4' atoms

| No. | W   | X        | Y    | Z   | Name                  | Reference |
|-----|-----|----------|------|-----|-----------------------|-----------|
| 1   | O   | O=P—O⁻   | O    | CH₂ | Phosphodiester (wild type) |      |
| 2   | O   | O=P—CH₃  | O    | CH₂ | Methyl phosphonate    | 1         |
| 3   | O   | O=P—OR   | O    | CH₂ | Phosphotriester       | 1         |
| 4   | O   | O=P—F    | O    | CH₂ | Phosphofluoridate     | 1         |
| 5   | O   | S=P—F    | O    | CH₂ | Phosphofluoridothionate | 1       |
| 6   | O   | O=P—NR₂  | O    | CH₂ | Phosphoramidate       | 1,6       |
| 7   | CH₂ | O=S=O    | CH₂  | CH₂ | Sulphone              | 1         |
| 8   | S   | CH₂      | O    | CH₂ | Thioformacetal        | 2         |
| 9   | CH₂ | CH₂      | S    | CH₂ | Thioether             | 3         |
| 10  | O   | O=S=O    | O    | CH₂ | Sulphate              | 3         |
| 11  | O   | O=S=O    | CH₂  | CH₂ | Sulphonate            | 3         |
| 12  | O   | O=S=O    | NH   | CH₂ | Sulphamate            | 3         |
| 13  | NH  | O=S=O    | CH₂  | CH₂ | Sulphonamide          | 3         |
| 14  | O   | S=O      | O    | CH₂ | Sulphite              | 3         |
| 15  | CH₂ | S=O      | CH₂  | CH₂ | Sulphoxide            | 3         |
| 16  | O   | R-Si-R   | O    | CH₂ | Siloxane              | 1,2       |
| 17  | O   | CH₂      | O    | CH₂ | Formacetal            | 1         |
| 18  | O   | O=C      | O    | CH₂ | Carbonate             | 1         |
| 19  | O   | O=C      | R-N  | CH₂ | Carbamate             | 1         |
| 20  | CH₂ | N—CH₃    | O    | CH₂ | N-methylhydroxylamine | 2,3       |
| 21  | R-N | O=C      | CH₂  | CH₂ | Amide                 | 2         |
| 22  | R-N | O=C      | R-N  | CH₂ | Urea                  | 2         |
| 23  | CH₂ | C=O      | CH₂  | CH₂ | Ketone                | 2         |
| 24  | CH₂ | CH₂      | CH₂  | CH₂ | Butyl                 | 2         |
| 25  | O   | CH₂      | O=C  | O   | Carboxymethyl         | 1         |

Example formulae (the references in superscripts are as for Table 1 itself) include:

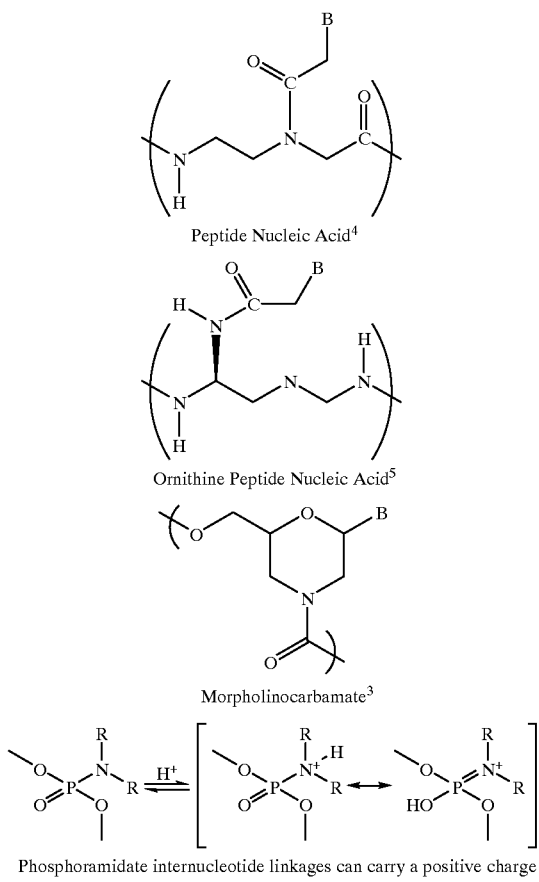

Peptide Nucleic Acid[4]

Ornithine Peptide Nucleic Acid[5]

Morpholinocarbamate[3]

Phosphoramidate internucleotide linkages can carry a positive charge

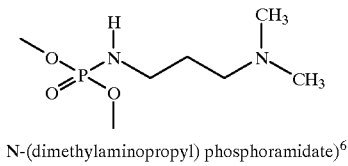

N-(dimethylaminopropyl) phosphoramidate[6]

References for Table 1
1. Protocols for Oligonucleotides and Analogs, Ed. S Agrawal, Humana Press, 1993.
2. A De Mesmaeker, R. Häner, P Martin and H E Moser, *Acc. Chem. Res.* (1995), 28, pp366–374.
3. J F Milligan, M D Matteucci and J C Martin, *J. Med. Chem.* (1993), 36, pp1923–1937.
4. M Egholm, O Buchardt, P E Nielsen and R H Berg, *J. Am. Chem. Soc.* (1992), 114, p1895.
5. E Lioy and H Kessler, *Liebigs Ann.* (1996), 201–204.
6. S Chaturvedi, T Horn and R L Letsinger, *Nucleic Acids Res.* (1996), 24, pp2318–2323.

The use of neutral internucleotide linkages to prepare modified nucleic acids is generally intended to confer resistance to the degradation of the nucleic acids by phosphodiesterases and alkaline phosphatases and also to increase their lipophilicity as an aid to crossing cell membranes when they are used as in-vivo therapeutics. However it is often found that the use of non-natural internucleotide linkages reduces the thermal stability of a duplex formed between the modified nucleic acid and its complementary, wild-type sequence. For this reason modified, neutral internucleotide linkages are often inserted into a nucleic acid only at its 3' and/or 5' termini in order to inhibit enzymic degradation while the remaining internucleotide linkages are phosphodiester groups which are used to maintain duplex stability.

Some of the neutral internucleotide linkages however are not found to be destabilising. These include some amide, N-methylhydroxylamine and thioformacetal linkages. Nucleic acids prepared with these linkages bind to RNA to form duplexes with the same or higher stability than that between wild-type DNA and RNA (see reference 2 following Table 1). Peptide nucleic acids (PNAs) also bind to DNA to form hybrids which are more stable than the corresponding DNA-DNA hybrids.

A SER(R)S probe, ie, a target binding species combined with a label for detection by the present invention, may be prepared from an appropriately labelled nucleic acid, the nucleic acid having been prepared either (i) using a mixture of wild type phosphodiester internucleotide linkages in combination with synthetic, neutral internucleotide linkages or (ii) entirely from synthetic, neutral internucleotide linkages, including PNA. Such a modified nucleic acid would be expected to be less acidic than the corresponding wild-type DNA or RNA sequence and would therefore show an increased affinity for a SER(R)S-active surface.

Especially useful as a SER(R)S probe would be one prepared using a phosphoramide internucleotide linkage. Of special potential utility are linkages which replace the (O⁻) functionality of a phosphodiester group with $NR_2$ to form phosphoramidates. Each modified linkage is then not merely neutral but also capable of carrying a positive charge. Chaturvedi et al (reference 6 following Table 1) have extended this concept by preparing N-(dimethylaminopropyl)phosphoramidates which carry an aliphatic amino group per internucleotide residue as well as the phosphoramidate amino function.

(iii) Chemi-sorptive functional group on the label

The SER(R)S-active label preferably incorporates a functional group which will promote its chemi-sorption onto the SER(R)S-active surface. The choice of such a group will depend on the nature of the surface (eg, its charge and the presence or absence of an oxide or other layer) and of any surface coatings or other species (such as citrate reducing agents) associated with it, and also on the nature of the label. For most useful surfaces, the functional group preferably comprises a Lewis base. Ideally, it is actively attracted to the surface in use.

The triazole group:

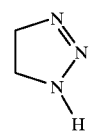

is rich in nitrogen lone pairs and seems to have a particular affinity for SER(R)S-active surfaces such as metal colloids. Thus, incorporation of this group in the label is particularly preferred, since it can increase the proximity of the label to the surface, the surface enhancement effect and, ultimately, the detection sensitivity.

The label preferably contains the benzotriazole group, particularly when the SER(R)S-active surface is silver- or copper-based:

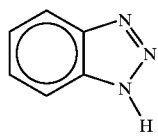

which has a high degree of conjugation (especially when deprotonated) and is thus particularly amenable to SERRS detection which relies on label resonance.

Benzotriazole derivatives, such as:

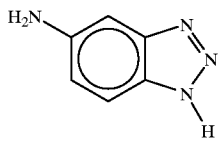

are readily available and can be coupled with existing labels (such as azo dyes, for instance) to give appropriately modified labels. Some such modified labels are thought to be novel compounds and as such, also form aspects of the present invention (see in particular the seventh aspect defined below).

Other suitable chemi-sorptive functional groups for the SER(R)S-active label include the calixerines and the mercapto benzotriazoles.

Suitable labels for use in the present invention include azobenzotriazoles, typically formed by combining azo substrates with benzotriazole derivatives. Examples of azobenzotriazoles include 9-(carboxyethyl)-3-hydroxy-6-oxo-6H-benzotriazole, and substituted benzoic and naphthoic acid azo derivatives coupled to benzotriazole.

Suitable labels are encompassed by the formulae:

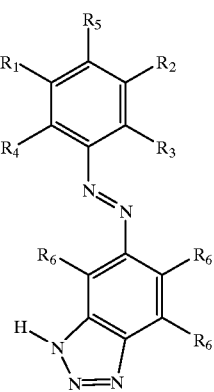

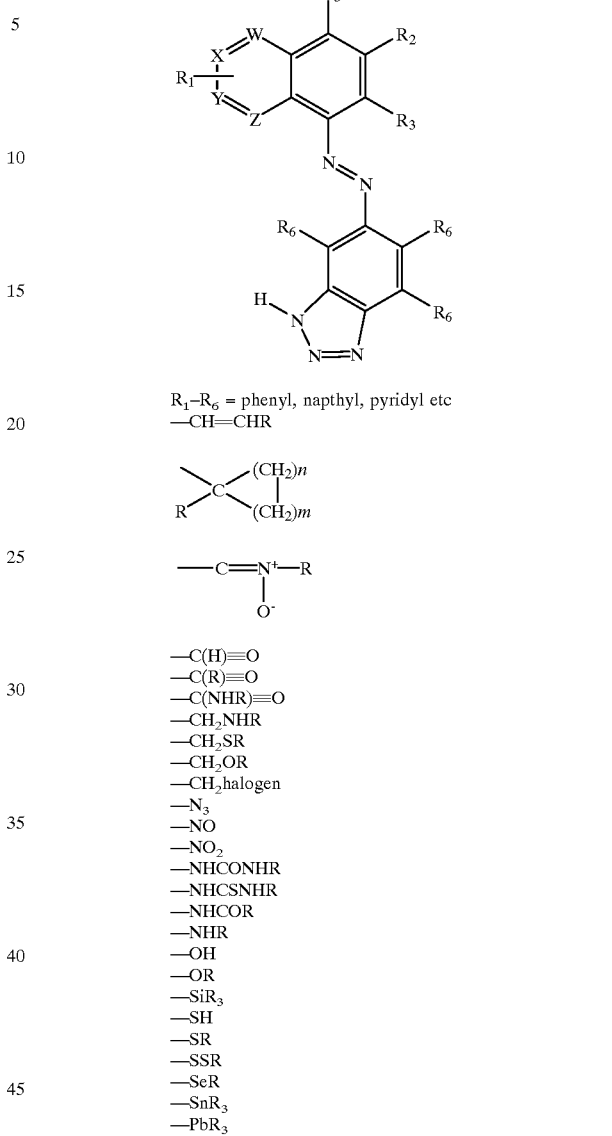

$R_1$–$R_6$ = phenyl, napthyl, pyridyl etc
—CH=CHR

—C=N$^+$—R
    |
    O$^-$

—C(H)=O
—C(R)=O
—C(NHR)=O
—CH$_2$NHR
—CH$_2$SR
—CH$_2$OR
—CH$_2$halogen
—N$_3$
—NO
—NO$_2$
—NHCONHR
—NHCSNHR
—NHCOR
—NHR
—OH
—OR
—SiR$_3$
—SH
—SR
—SSR
—SeR
—SnR$_3$
—PbR$_3$ where R = H or any alkyl, aryl group
W, X, Y, Z = C, O, S or N
n, m = any integer > 1 in which $R_1$–$R_6$ represent any appropriate groups (including hydrogen), of which examples will be well known to the skilled person, but preferably those listed to the right of the formulae. W, X, Y and Z are also defined to the right of the formulae. A more preferred sub-set of such compounds is those in which $R_1$, $R_2$, $R_3$, $R_4$ and $R_6$ are independently selected from hydrogen, $C_1$–$C_6$ alkyl, $C_1$–$C_6$ alkoxy, 6-membered aromatic rings, halogen, —COOH, —SO$_3$H, —PO$_4$, —SH, —PO, —NR$_7$ and $R_8$; $R_5$ can be as $R_1$ or alternatively —NH$_2$ or functionalised —COOH such as —(CH$_2$)$_n$—COOH where n is an integer from 1 to 6; and $R_7$ and $R_8$ are independently selected from hydrogen, $C_1$–$C_6$ alkyl (linear or branched chain) and unsaturated cyclic alkyl rings.

Most preferred forms of such labels are those in which $R_1$ and $R_2$ are both hydrogen, $R_3$ and $R_4$ are independently selected from hydrogen and methoxy, $R_5$ is either —COOH or —amino and $R_6$ is hydrogen. Yet more preferred are those referred to in Example 2 below.

Practical considerations

Other features of the first and second aspects of the invention may be entirely conventional. For instance, the immobilisation, isolation and/or manipulation of the target and the label-containing complexes, if desired; and the use and interpretation of the SER(R)S spectrum obtained (especially if it is to be used as part of an overall sequencing method) can all be carried out according to practices well known to the person skilled in the art.

It should also be noted that, in order to maximise detection sensitivity, the user needs to select appropriate features—label, label modification, target binding species if appropriate, nucleic acid modification, polyamine, light source, etc. . . . , and in particular the SER(R)S-active surface—which interact in the most effective possible manner given all the circumstances of the use. This selection may in part be a process of trial-and-error adjustment of reagents, conditions and other parameters, but it will be well within the capabilities of the person of average skill in the art, provided he makes use of the guidance contained in this document.

Careful choice of label(s) and light source(s) can also enable (using SERRS) the highly selective detection of several targets together by means of their distinguishing Raman spectra, without the need for prior separation. Possibly up to twenty different SERRS-active labels could be resolved in this way, ideally in a homogeneous array of the type described below.

Homogeneous and non-homogeneous assays

The detection sample may be in a solid, liquid or gaseous format. The methods of the invention are conveniently carried out in a homogeneous format, ie, all the required reagents are added to the detection sample simultaneously or substantially so and a result is obtained without the need to add further reagents at any stage or subsequently to separate any component of the test from the remaining components.

Homogeneous assays have the advantage that they are less prone to contamination, and less likely themselves to contaminate the external environment, since reaction vessels do not need to be opened at any time during the assay. The direct detection of nucleic acids and nucleic acid units without amplification, as in the present invention, is not prone to contamination by the products of previous assays as can occur in amplification based assays. Nevertheless the high sensitivity required in the methods of the invention makes it desirable that they be conducted in homogeneous systems.

Known examples of homogeneous nucleic acid assays tend to be based on fluorescence spectroscopy. The present invention now makes it possible to use the potentially much simpler and less costly SER(R)S spectroscopy to carry out similar types of assays.

Homogeneous assays, in accordance with the present invention, can conveniently be carried out using evanescent wave detectors—see the description below of suitable light sources for use in the invention.

Obtaining the SER(R)S spectrum

The method for obtaining the SER(R)S spectrum, once the label-containing primary or secondary complex has been formed, may also be conventional. The present invention is merely concerned with chemical modifications to existing SER(R)S techniques, ie, modifications to the target or target binding species, the label and the SER(R)S-active surface, to make them viable for use in detecting unamplified nucleic acid-based targets.

By way of example, however, the following might apply to the spectroscopic measurements:

Light source

Typically, the methods of the invention will be carried out using incident light from a laser, having a frequency in the visible spectrum (the exact frequency chosen will depend on the label, surface and target in each case—frequencies in the red area of the visible spectrum tend, on the whole, to give rise to better surface enhancement effects). However, it is possible to envisage situations in which other frequencies, for instance in the ultraviolet or the near-infrared ranges, might be used—see the discussion below regarding sequencing methods.

The selection and, if necessary, tuning of an appropriate light source, with an appropriate frequency and power, will be well within the capabilities of one of ordinary skill in the art, particularly on referring to the available SER(R)S literature. To achieve highly sensitive detection, using SERRS, a coherent light source is needed with a frequency at or close to the absorption maximum for the label (as described above) or that of the surface plasmons. If lower sensitivities are required, the light source need not be coherent or of high intensity and so lamps may be used in combination with a monochromator grating or prism to select an appropriate excitation frequency; here, there is no need to operate at the resonant frequency of the label or the plasmons.

The source can be used to excite the label directly on an active surface such as an electrode; by shining through a SER(R)S-active colloidal suspension; or by means of evanescent waves via a waveguide coated with a SER(R)S-active surface.

The light can be conducted from the source to the active surface by reflection in mirrors and can be focussed to give a higher light flux by passing through lenses. A suitable apparatus for SER(R)S analyses is a fluorescence microscope with signal detection at 90° to the excitation beam. A fluorescence microscope with confocal optics is also appropriate. The use of microscope optics permits very small areas or volumes to be analysed.

The light can alternatively be conducted from the source to the active surface through a waveguide. This gives flexibility as to the site of sampling; the waveguide can be scanned over the active surface or dripped into a SER(R)S-active colloid suspension. A waveguide is particularly appropriate for use in analyses carried out in the solution phase in the wells of a microtitre plate. The waveguide can be carried on a robot arm and deposited sequentially in each well for high throughput screening of many samples.

A waveguide coated with a SER(R)S-active surface may also be used selectively to detect analytes which bind to that surface. The principle is as follows. Light is passed along a waveguide by total internal reflection. However, molecules closely bound to the external surface of the waveguide may still be excited by the electric field of the light ("evanescence"). Emissions, such as SER(R)S emissions, resulting from this excitation pass on through the waveguide and can be detected at its output end.

A SER(R)S spectrum detected in this way will be affected if the surface molecules become bound to other species. It can thus reveal the presence of binding, say, between affinity pairs such as a target nucleic acid and its complementary target binding species, one half of the pair being coated onto the waveguide surface to "capture" the other half from a sample. Naturally, a SER(R)S-active label is necessary on at least one of the two halves of the pair. Preferably, the "free" half is labelled, so that SER(R)S signals will only be detected when that species is "captured" by its complementary species on the waveguide surface. Because only molecules that are bound to the waveguide surface are interrogated, specific binding events can be detected homogeneously without the need to wash away unreacted reagents.

Several publications disclose suitable methods for coating optical fibres so that they specifically absorb analytes to permit their subsequent SER(R)S detection. U.S. Pat. No. 4,395,312 (McCreery et al) discloses electrochemical generation of chromophores that can be detected by Raman probes. U.S. Pat. No. 4,573,761 (McLachlan et al) discloses a fibre optic probe comprising separate transmitting and collecting optical fibres useful for Raman spectroscopy which have a specially designed angle of convergence. U.S. Pat. No. 4,781,458 (Angel et al) discloses an optical fibre probe, or "optrode", thinly coated with a SERS-active metal and additionally coated on one side, over the metal, with a selectively absorbent material. U.S. Pat. No. 4,834,497 (Angel et al) also discloses a fibre-optic fluid detector designed for specific materials such as gasoline. U.S. Pat. No. 5,327,211 (Carron and Mullen) discloses a method for producing optical fibres or fibre-optic probes coated with a chemical layer that selectively complexes or partitions desired molecules, allowing SERS detection.

Detector

In SER(R)S the primary measurements are of the intensity of the scattered light and the wavelengths of the emissions. Neither the angle of the incident beam nor the position of the detector is critical. With flat surfaces an incident laser beam is often positioned to strike the surface at an angle of 60° with detection at either 90° or 180° to the incident beam. With colloidal suspensions detection can be at any angle to the incident beam, 90° again often being employed.

The intensity of the Raman signals needs to be measured against an intense background from the excitation beam, and for this reason the use of Raman analytes with large Stokes' shifts is an advantage. The background is primarily Raleigh scattered light and specular reflection, which can be selectively removed with high efficiency optical filters.

Several devices are suitable for collecting SER(R)S signals, including wavelength selective mirrors, holographic optical elements for scattered light detection and fibre-optic waveguides. The intensity of a SER(R)S signal can be measured using a charge coupled device (CCD), a silicon photodiode, or photomultiplier tubes arranged either singly or in series for cascade amplification of the signal. Photon counting electronics can be used for sensitive detection. The choice of detector will largely depend on the sensitivity of detection required to carry out a particular assay.

Note that the methods of the invention may involve either obtaining a full SER(R)S spectrum across a range of wavelengths, or selecting a peak and scanning only at the wavelength of that peak (ie, Raman "imaging").

Data processor

Apparatus for obtaining and/or analysing a SER(R)S spectrum will almost certainly include some form of data processor such as a computer.

Raman signals consist of a series of discrete spectral lines of varying intensity. The frequencies and the relative intensities of the liens are specific to the label being detected and the Raman signal is therefore a "fingerprint" of the label. If a SER(R)S analyzer is being used selectively to detect one label out of a mixture then it will be necessary to detect the entire "fingerprint" spectrum for identification purposes. However if the analyzer is being used to quantitate the detection of one or several labels, each of which has a unique spectral line, then it will only be necessary to detect signal intensity at a chosen spectral lien frequency or frequencies.

Once the SER(R)S signal has been captured by an appropriate detector, its frequency and intensity data will typically be passed to a computer for analysis. Either the fingerprint Raman spectrum will be compared to reference spectra for identification of the detected Raman active compound or the signal intensity at the measured frequencies will be used to calculate the amount of Raman active compound detected.

Instrumentation

A commercial SER(R)S analyzer of use in carrying out the invention would be expected to consist of the following components: a laser light source, the appropriate optics for carrying the light to the SER(R)S active surface, a stage for mounting the sample for analysis, optics for receiving the Raman signal, a detector for converting the Raman signal into a series of intensities at certain wavelengths and a data processor for interpreting the wavelength/intensity data and providing an analytical output.

The light source, optics, detector and processor have already been referred to. The stage for mounting the sample could be designed to accommodate one or more of the following solid supports: a microscope slide or other flat surface such as a silicon wafer or chip, a microtitre plate or a higher density array microwell plate, or a membrane.

An assay could be carried out on a solid support and the support inserted into a SER(R)S reader for analysis. Alternatively the assay could be carried out in a separate vessel with a subsequent transfer of the assay components to the solid support for inserting into the analyzer. The use of robotics to transfer solid supports to and from a SER(R)S analyzer stage would permit the development of a high throughput system without significant operator input with samples being run and analysed automatically.

Third and fourth aspects—complexes

According to a third aspect, the present invention provides a SER(R)S-active complex comprising a target nucleic acid or nucleic acid unit bound to a SER(R)S-active label, optionally via a target binding species containing a nucleic acid or nucleic acid unit, the label being associated with a SER(R)S-active surface, and the complex incorporating one or more, preferably all three, of the features (i)–(iii) described above.

According to a fourth aspect, the invention provides a SER(R)S-active complex comprising a binding species which contains a nucleic acid or nucleic acid unit and is bound to a SER(R)S-active label, the label being associated with a SER(R)S-active surface, and the complex incorporating one or more, preferably all three, of the features (i)–(iii) described above.

Such complexes are naturally of use in methods according to the first and second aspects of the invention. In the fourth aspect, the binding species will typically be a probe or primer which is substantially complementary to at least a part of another nucleic acid or nucleic acid unit which, ultimately, it is desired to detect. Such a complex could be reacted, for example, with an immobilised target in a sample; unbound complex could then be washed away so that any label-containing complex remaining would be indicative of the presence of the target in the original sample.

Binding of the constituent species of these complexes, to one another, may be by association or by a direct or indirect (through a linking group) chemical bond such as a covalent or chelating bond.

"Incorporation" of feature (i) means that a polyamine is associated with the complex, eg, in the form of a charge-balancing ion pair with all or part of the target or binding species, and/or of a coating on the SER(R)S-active surface.

Fifth aspect—sequencing

The invention further provides, according to a fifth aspect, a method for sequencing a nucleic acid which comprises the use of the method of the first or the second aspect to detect at least one target nucleotide or sequence of nucleotides within the acid. Other steps in such a sequencing method may be entirely conventional; the skilled person will be readily able to make use of data from the method of the first or second aspect of the invention in order to reach a conclusion as to an overall sequence. In this method, the SER(R)S-active label may be complexed to the relevant target nucleotide or sequence via a target binding species in the form of a nucleic acid primer sequence substantially complementary to that target, or in the form of a dNTP or ddNTP
((di) deoxynucleotidetriphosphate base).

Current non-radioactive protocols for nucleic acid sequencing have been based around two main systems:

a) Four identical primers labelled with different dyes are run in "Sanger" type chain termination reactions, pooled and resolved by gel electrophoresis. The fluorescence is detected in the gel using a laser and CCD.

b) Each dideoxy terminator base in a Sanger reaction is labelled with a different dye and all the reactions are run in a single pot. After removal of excess dye terminator reagent, the labelled products are resolved by gel electrophoresis and interrogated by laser.

In order to discriminate between the dyes a range of excitation and emission wavelengths are used which limits the sensitivity that can be achieved with a single laser line since some of the dyes have excitation maxima well away from that used. In addition, a good quantity of sequencing template is required to obtain reliable information, usually necessitating prior amplification with its resultant inconvenience and cost. Thus, use of the methods of the present invention in sequencing techniques offers considerable advantages.

Using the present invention, both of the above reaction schemes are possible. Other detection schemes might be direct blotting of the sequencing extension products onto nylon or nitrocellulose membranes, or elution of the products from gel electrophoresis onto a moving roll of membrane. The products could then be detected by soaking with polyamine (eg, spermine) followed by colloid and SER(R)S spectroscopy of the whole filter. Two main gains derive from the use of the present invention in sequencing: firstly, each dye can have excitation optima very close to the laser line so all are excited equally well and secondly, the high sensitivity of the method of the invention allows smaller quantities of starting template to be used, with the potential for sequencing directly from the genome.

A plausible sequencing format, in accordance with the fifth aspect of the invention, might be:

a. isolate template (or possibly genome).

b. using four parallel reactions with a different labelled primer and ddNTP terminator in each, carry out chain termination sequencing.

c. pool the four reactions.

d. resolve the reaction products on a polyacrylamide/urea gel.

e. blot the gel onto nylon.

f. soak the membrane with spermine.

g. soak the membrane with dispersed silver colloid.

h. obtain SER(R)S spectra.

i. reconstitute a sequence from the image which may be processed.

An alternative sequencing scheme would be akin to Southern blotting. Four terminator reactions are run with no labelling. After electrophoresis (four lanes per template), the products are transferred to a membrane and hybridised to a complementary probe carrying a SER(R)S-active label. The SER(R)S signal is developed by soaking in spermine and colloid before collecting spectra. Throughput in such a reaction could be improved by performing multiple reactions and using the probes to "see" only one reaction set at a time. The hydridisations with the various probes could be sequential or simultaneous (relying on sophisticated decoding of the data by computer software). Probes would be near the priming site but internal to the sequenced region.

A sequencing method in accordance with the invention may also involve multiplexing (see Example 9 below).

Sequencing in the ultra violet range

Further disadvantages of conventional nucleic acid sequencing techniques (based on the "Sanger" method) include (i) the need to run four separate sequencing reactions, one for each base, and (ii) the need to analyse the results using high resolution electrophoresis.

A technique currently under investigation (SEQ), which addresses some of these issues, requires a single molecule of a nucleic acid to be tethered to a solid support in a linear flow of buffer and to be treated with a 3' to 5' exonuclease under controlled conditions. Each nucleotide is cleaved from the nucleic acid sequentially and flows past an appropriate detector.

At this point, a detection method in accordance with the present invention could be used to detect the presence of the individual nucleotides and hence provide a sequence listing for the original nucleic acid. In this case, the SER(R)S spectrum would ideally be obtained using incident light in the ultra violet range and a surface having appropriate SER(R)S activity. There are several advantages to such a technique. Firstly, each of the four nucleotides has a similar UV spectrum (one maximum at approximately 260 nm), so each would be maximally excited by a single laser line centred at this frequency. It would also be expected that, as is usual with Raman spectroscopy, the four nucleotides would have readily distinguishable Raman spectra. Finally, the UV extinction coefficients of nucleotides are very high, making them very detectable using SER(R)S.

The possibility of using Raman resonance spectroscopy in the UV range for analysis of biological samples is referred to briefly by T M Cotton et al in *J. Raman Spectroscopy* (1991), 22, pp729–742. A UV-based technique would probably be used to detect a nucleic acid or nucleic acid unit directly by means of its SER(R)S spectrum, rather than via a separate SER(R)S-active label. The target nucleic acid (unit), or an appropriate target binding species, would in this case also function as the SER(R)S-active label.

Sixth aspect—kit

According to a sixth aspect, the invention provides a kit for use in carrying out a method according to the first, second or fifth aspects or for forming a complex according to the third or fourth aspect. Such a kit will comprise at least a SER(R)S-active label or means for preparing such a label, and preferably a SER(R)S-active surface or means for preparing such a surface. The label may already be bound to, or otherwise associated with, the surface or a reagent used to prepare the surface. The label may additionally or alternatively be bound to a target binding species such as an oligonucleotide or PNA probe, designed to react with a target of interest. The key may if appropriate include a surface-label-binding species complex in accordance with the fourth aspect of the invention.

The label is preferably modified according to feature (iii) of the invention. Any target binding species present is preferably modified according to feature (ii). In accordance with feature (i), the kit also preferably includes a polyamine for introduction into a detection sample prior to obtaining a SER(R)S spectrum.

Means for preparing a SER(R)S-active surface might comprise, for example, reagents such as citric acid, silver nitrate, ascorbic acid, distilled water and spermine (for the preparation of a silver colloid).

A kit in accordance with the invention may also include a capture material, by means of which a target or a label-containing complex could be immobilised on a solid support. An appropriate capture material might be an oligonucleotide probe (ie, a target binding species) attached to, or capable of being specifically attached to, a solid support. Such a support could be, for instance, the surface of a microtitre plate, a paramagnetic bead or a sedimentable bead.

The kit may also include reagents and/or other materials (eg, filters, syringes, columns, etc. . . . ) for preparing a crude target-containing sample for SER(R)S analysis. It may include reagents, such as enzymes, for use in the manipulation of target nucleic acids or nucleic acid units and/or of other reagents. Such enzymes are well known in the art and include, for example, Taq polymerase and other high fidelity nucleic acid polymerases.

Finally, the kit may contain apparatus for use in obtaining a SER(R)S spectrum, such as a light source, detector, data processor, etc. . . . It may contain a waveguide coated with a SER(R)S-active surface, optionally with a target binding species also bound to that surface.

Seventh aspect—novel compounds

Finally, according to a seventh aspect, the present invention provides the following novel azobenzotriazoles which are of use as SER(R)S-active labels in other aspects of the invention:

a) 3-methoxy-4-(5'-azobenzotriazolyl)-phenylamine;
b) 3,5-dimethoxy-4-(5'-azobenzotriazolyl)-phenylamine; and
c) 4-(5'-azobenzotriazolyl)-1-aminonaphthalene.

Sensitivity of the methods of the invention

Experiments have shown that methods according to the first and second aspects of the invention are capable of detecting sub-femtomolar ($10^{-15}$ M) quantities of target nucleic acids such as DNA, RNA, cDNA, mRNA and the like—no prior amplification of the target is necessary. Using a target molecule of 17–18 bases, labelled with a single dye molecule, the presence of between 1 and 100 (almost certainly less than 50) target molecules has been reliably detected in the solid phase; in the solution phase, between 1 and 10 molecules have been detected (see also Examples 5, 7 and 8 below).

A sequencing method in accordance with the fifth aspect of the invention can generally be carried out using lower quantities of the required template sequence than are needed for conventional sequencing techniques—typically less than about 100 femtomoles of template will suffice, possibly even of the order of attomolar ($10^{-18}$ M) quantities or less.

The high sensitivity of the methods of the invention is due to the ability of the label-containing SER(R)S-active complex to approach very close to the SER(R)S-active surface; surface-label separations of the order of 5 Å, much lower than the 20 nm necessary for a SER(R)S effect, are possible using the methods of the invention.

Uses of the invention

The uses of the invention will be clear from the above description and include the prediction and detection of medical conditions, forensic testing, the sequencing of human and animal genes and identification of security-tagged products, the "tag" comprising a target nucleic acid or nucleic acid unit. Other techniques which involve the detection of genetic markers, and in which the present invention could therefore be of use, include the detection of positive traits in foodstuff and livestock breeding and the detection of HLA specificities to permit the matching of transplant samples. Clearly, aspects of the invention may be used to detect high as well as low concentrations of a target nucleic acid or nucleic acid unit.

Detection methods according to the invention may be used to improve on a whole range of existing biochemical techniques. Sequencing (as described in connection with the fifth aspect of the invention) is an obvious example. Others are outlined below.

A) Genetic disease, acquired or inherited, arises when the DNA sequence of an organism's genome varies from the wild-type sequence at certain crucial points. Analysis of this variation is currently carried out using sequencing, SSCP and DGGE to analyse DNA which has been amplified by the PCR, or other amplification based techniques. The use of ARMS (EP-B-3,332,435) is useful for generating a PCR product in a sequence dependent manner which precludes the need subsequently to analyse the sequence of the amplified fragment. Direct analysis of genetic disease by using ARMS to generate linear extension products from genomic DNA, with subsequent detection of the extension using the method of the present invention, would speed genetic analysis. Avoiding PCR amplification would also prevent the risk of PCR product crossover contamination. The use of ARMS to detect sequence variation is not limited to mutations associated with disease states but could also be applied to detecting single nucleotide polymorphisms (SNPs) which are silent mutations useful in distinguishing individuals genetically.

B) Variable numbered tandem repeat (VNTR) analysis is a means of identifying individuals based on genetic variability from person to person. Genomic DNA is treated with restriction enzymes to generate DNA fragments, some of which contain tandem repeat sequences of variable length. These fragments are separated by electrophoresis and the gel is denatured with alkali. The DNA is then transferred to a membrane and a labelled single stranded oligonucleotide probe complementary to the repeat sequence is hybridised to the DNA. After the probe has been subjected to a stringency wash it is detected via its label. For example, probes labelled with the enzyme alkaline phosphatase might be detected by their generating chemiluminescence from a suitable phosphorylated substrate or radiolabelled probes could be detected by autoradiography. Once the probe has been detected it is stripped off and the next probe is hybridised in order to detect another VNTR. Usually three to five probings are carried out per individual and each probing takes a working day. The probes are not multiplexed because enzyme-linked detection and autoradiography do not lend themselves to such multiplex detection and fluorescent probing is not sensitive enough due to the small amounts of input DNA and the high autofluorescene of hybridisation membranes. It would be an advantage in reducing operator time if all the probings could be carried out simultaneously. The methods of the present invention would allow the multiplex detection of several probes with their unique Raman vibrational "fingerprints" without the problem of autofluorescent backgrounds.

C) Difficulties in multiplexing fluorescence are also observed in the field of cytogenetic analysis by Fluorescence In-Situ Hydridisation (FISH). Due to the broad fluorescence of most organic fluorophores it is difficult to select more than five visible fluorophores whose fluorescence does not overlap so that many cytogenetics laboratories use only two or three fluorophores to label their chromosome probes which limits multiplex detection. One solution is to use varying mixtures of fluorophores to colour different chromosome regions with sequential detection of each colour with a separate filter and computer merging of the resulting images to identify each differently labelled region. This technique requires expensive imaging and analysis equipment and the technique is used by relatively few laboratories. It would be advantageous to use the discrete spectral lines of Raman spectra to allow different chromophores to be "fingerprinted" by hybridisation to different SER(R)S-active probes. A further advantage of such a technique is that Raman signals do not autoquench so that labelling chromophores can be packed more densely onto the chromosome surface than can fluorophores, with a corresponding build-up of signal.

D) Mini-sequencing, whereby a labelled dideoxy chain terminator is incorporated at the 3' terminus of a primer in a sequence dependent manner, may also be carried out directly on the genome with detection of the incorporated base by a method according to the present invention.

E) Analysis of the genes being expressed in tissues at various stages of the cell cycle by the detection of mRNAs is a useful means of tracking gene function. Currently mRNA levels are quantified by RT-PCR which is a difficult technique. Direct quantification of mRNA levels using the present invention would allow the rapid and simultaneous monitoring of many genes in tissues leading to insights into their function. This could be achieved by hybridising a probe labelled with a SER(R)S-active dye to an accessible region of the mRNA, then capturing the hybrid with a polythymidine sequence on a solid phase with subsequent quantification of the mRNA levels by measuring the intensity of the SER(R)S signals from the dye.

F) A further use of the invention is in detecting which regions of the mRNA are accessible to hybridisation to antisense oligonucleotides. mRNA has considerable secondary structure which can be predicted by computer modelling although this method is not satisfactory. Only certain regions of the mRNA are liable to be both single stranded and accessible for binding to an antisense oligonucleotide. It would be of considerable value to companies developing "antigene" technology to be able to identify these binding sites rapidly. One possible method is to bind the mRNA to a solid support on an array with $4^n$ elements where n is the length of an oligonucleotide probe (there would be $4^n$ possible oligonucleotide n-mers). The $4^n$ different probes would be prepared and labelled with a SER(R)S-active dye and then each would be added individually to a spot on the mRNA array and then subjected to a stringency wash. Those labelled probes which hybridise to the mRNA would be detected by SER(R)S spectroscopy and reference to the mRNA sequence would reveal which regions of the molecule were available for probing. Once prepared, the resultant library of SER(R)S probes could be used for any desired mRNA target. Alternatively the $4^n$ probe oligomers could be plated out on an oligonucleotide array as is well known in the art and the mRNA could be added and subjected to a stringency wash. Binding of the mRNA to specific regions of the array could be detected by adding a polythymidine probe labelled with a SER(R)S-active dye which would bind to the polyA tail of the mRNA and be detected by SER(R)S. After completion of the analysis the mRNA could be removed by treatment with an RNAse or alkali and the array reused.

G) The use of oligonucleotide arrays in combination with the present invention can also be extended to analysing genotypes both for SNPs and for deleterious mutations. This can be done using amplified nucleic acids or, preferably, directly on unamplified material. A large number of capture probes for specific regions of the genome can be used to prepare the array and in theory a considerable amount of information concerning an individual's genetic variation could be collected in one experiment allowing that person to be uniquely identified (by SNPs) and giving clinically useful insights into their current and future disease state.

BRIEF DESCRIPTION OF THE DRAWINGS

The present invention will now be described in more detail with reference to examples and to the accompanying illustrative drawings, of which.

DETAILED DESCRIPTION

EXAMPLE 1

Figure 1:
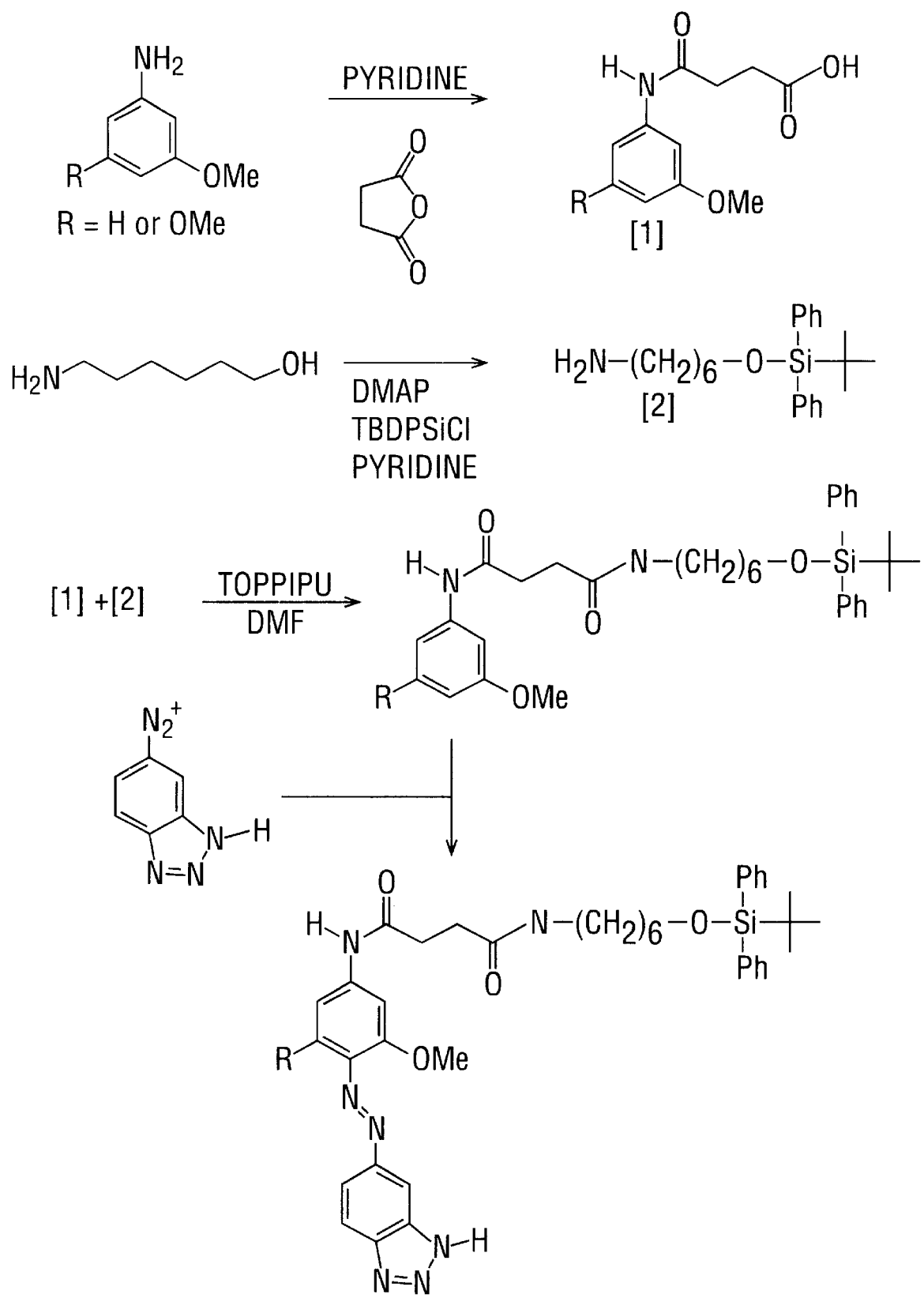
FIGS. 1 and 2 show alternative reaction schemes for preparing benzotriazole monoazo dyes for use as labels in a method according to the invention (Example 2)

Preparation of benzotiazole azo dyes - General procedure

Benzotriazole azo dyes, suitable for use as labels in the present invention, may be prepared according to the following general procedure.

Step 1: Diazotiasation 5-aminobenzotriazole (1.0 g, 7.63 mmol) is dissolved in HCl (5 ml, 50% v/v) and diazotised by dropwise addition of sodium nitrite (0.578 g, 1.1 eq, in 5ml $H_2O$) at 0° C. An excess of sodium nitrite is detected using starch iodide paper. A dark blue colour indicates the formation of the diazonium salt.

Step 2: Coupling reaction

The desired coupling agent (1 eq), to be coupled with the diazonium salt, is dissolved in sodium acetate buffer (5 ml, pH 6.0) and either acetone or dimethylformamide (10 ml). The diazonium solution is added dropwise to the buffered coupling agent. The solution is stirred at room temperature for 1 hour.

EXAMPLE 2

Preparation of benzotriazole azo dyes - Specific examples

A) 4-(5'-azobenzotriazolyl)-phenylamine Aniline (1 eq) was dissolved in sodium acetate buffer (1.0M, 5 ml, pH 6.0) and acetone (5 ml). Diazotised aminobenzotriazole was added to this solution dropwise at 0° C. with stirring over 1 hour. The solid produced was isolated by filtration and washed with saturated KCl (3×50 ml) to leave a dark yellow residue (0.892 g, 3.74 mmol, 84%), $R_f$ [dichloromethane/methanol (A) 9/1] 0.37; $\delta_H$ (DMSO-d6) 4.10 (1H, s, NH) 7.14–8.25 (7H, m, ar) 12.73 (2H, br s, $NH_2$) ; $\lambda_{max}$(MeOH) 360 nm.

B) 3-methoxy-4-(5'-azobenzotriazolyl)-phenylamine Anisidine (1 eq) was dissolved in sodium acetate buffer (1.0M, 5 ml, pH 6.0) and acetone (5 ml). Diazotised aminobenzotriazole was added to this solution dropwise at 0° C. with stirring over 1 hour. The solid produced was isolated by filtration and washed with saturated KCl (3×50 ml). The residue was recrystallised from ethanol/water (8:2) to yield red crystals (0.458 g, 1.94 mmol, 73%), $R_f$(A) 0.42; $\delta_H$ (DMSO-d6) 3.96 (3H, s, $OCH_3$) 6.46 (1H, s, ar) 6.60–6.63 (2H, d, ar) 6.63–7.68 (2H, br s, $NH_2$) 7.66–7.68 (1H, d, ar) 7.96–8.02 (2H, dd, ar) 8.18 (1H, s, ar); $\lambda_{max}$ (MeOH) 409 nm.

C) 3,5-dimethoxy-4-(5'-azobenzotriazolyl)-phenylamine 3,5-dimethoxyaniline (1 eq) was dissolved in sodium acetate buffer (1.0M, 5 ml, pH 6.0) and acetone (5 ml). Diazotised aminobenzotriazole was added to this solution dropwise at 0° C. with stirring over 1 hour. The solid produced was isolated by filtration and washed with saturated KCl (3×50 ml). The residue was recrystallised from methanol to yield orange crystals (0.768 g; 2.58 mmol, 67%), $R_f$ (A) 0.37; $\delta_H$ (DMSO-d6) 3.36 (6H, s, $2 \times OCH_3$) 3.87 (2H, s, ar) 6.08 (2H, s, ar) 7.81 (3H, m, $NH_2$+ar) 11.99 (1H, s, NH); $\lambda_{max}$ (MeOH) 395 nm; FAB ms m/z 299.1256 [$C_{14}H_{14}O_2N_6$(M+1) <0.1 ppm].

D) 4-(5'-azobenzotriazolyl)-1-aminonaphthalene 1-aminonaphthalene (1 eq) was dissolved in sodium acetate buffer (1.0M, 5 ml, pH 6.0) and acetone (5 ml). Diazotised aminobenzotriazole was added to this solution dropwise at 0° C. with stirring over 1 hour. The solid produced was isolated by filtration and washed with saturated KCl (3×50 ml). The residue was recrystallised from water to yield violet crystals (0.645 g, 2.24 mmol, 29%), $R_f$(A) 0.35; $\delta_H$ (DMSO-d6) 3.36 (6H, s, $2 \times OCH_3$) 3.87 (2H, s, ar) 6.08 (2H, s, ar) 7.81 (3H, m, $HN_2$+ar) 11.99 (1H, s, NH); $\lambda_{max}$ (MeOH) 469 nm.

Other synthesis schemes for benzotriazole monoazo dyes Initially, the scheme outlined in FIG. 1 was attempted in order to prepare benzotriazole monoazo dyes suitable for use as labels in the invention. However, the coupling of the aromatic ring to the benzotriazole proved to be a very difficult reaction. The activity of the 4-position was greatly reduced due to the presence of the amide linkage. The reaction was attempted using three different aromatic rings. Unfortunately all proved difficult to achieve.

Figure 2:
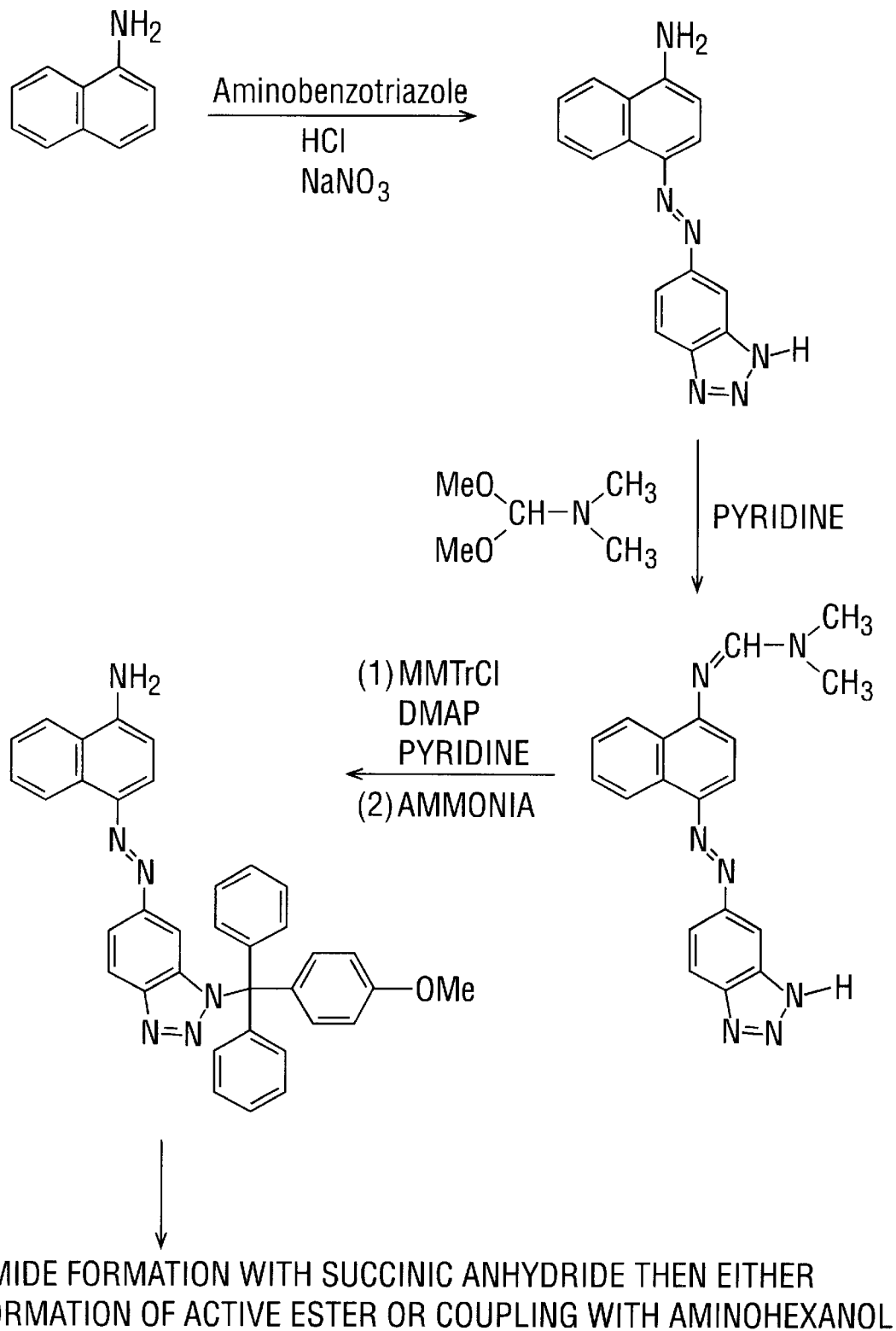
Figure 3:
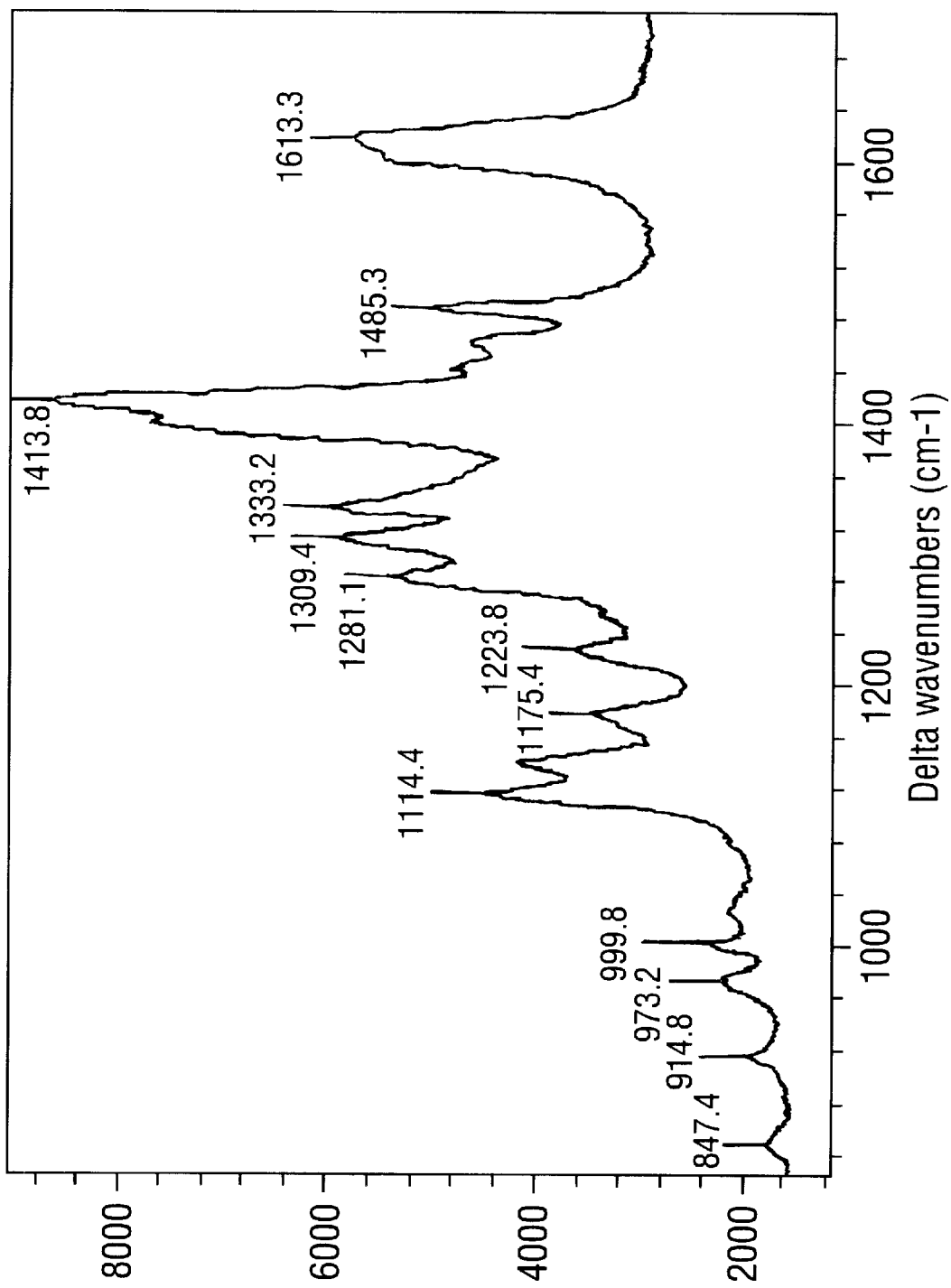
FIGS. 3–6 are SERRS spectra for modified azo dyes of use as labels in a method according to the invention (Example 3)
Figure 4:
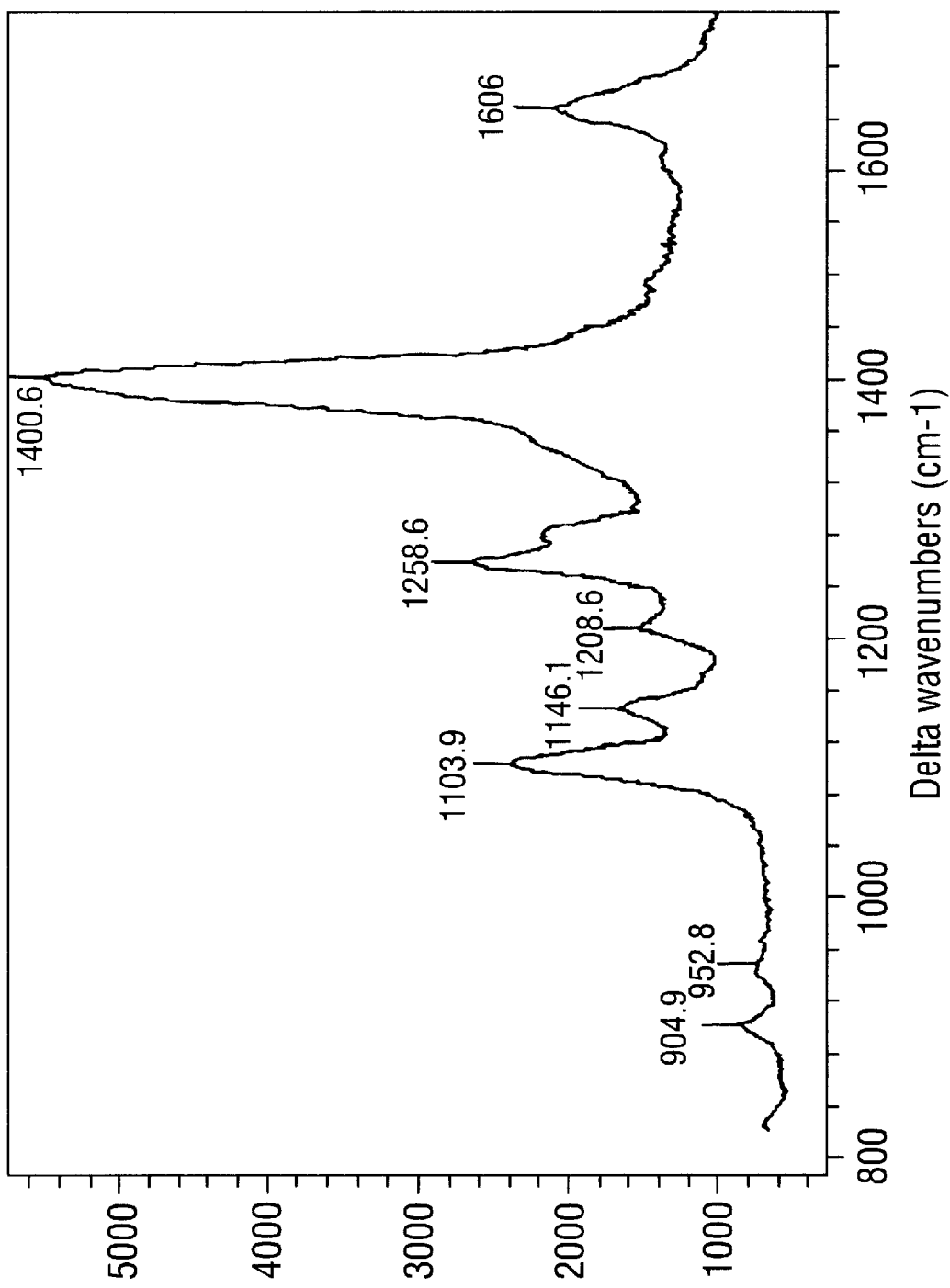
Figure 5:
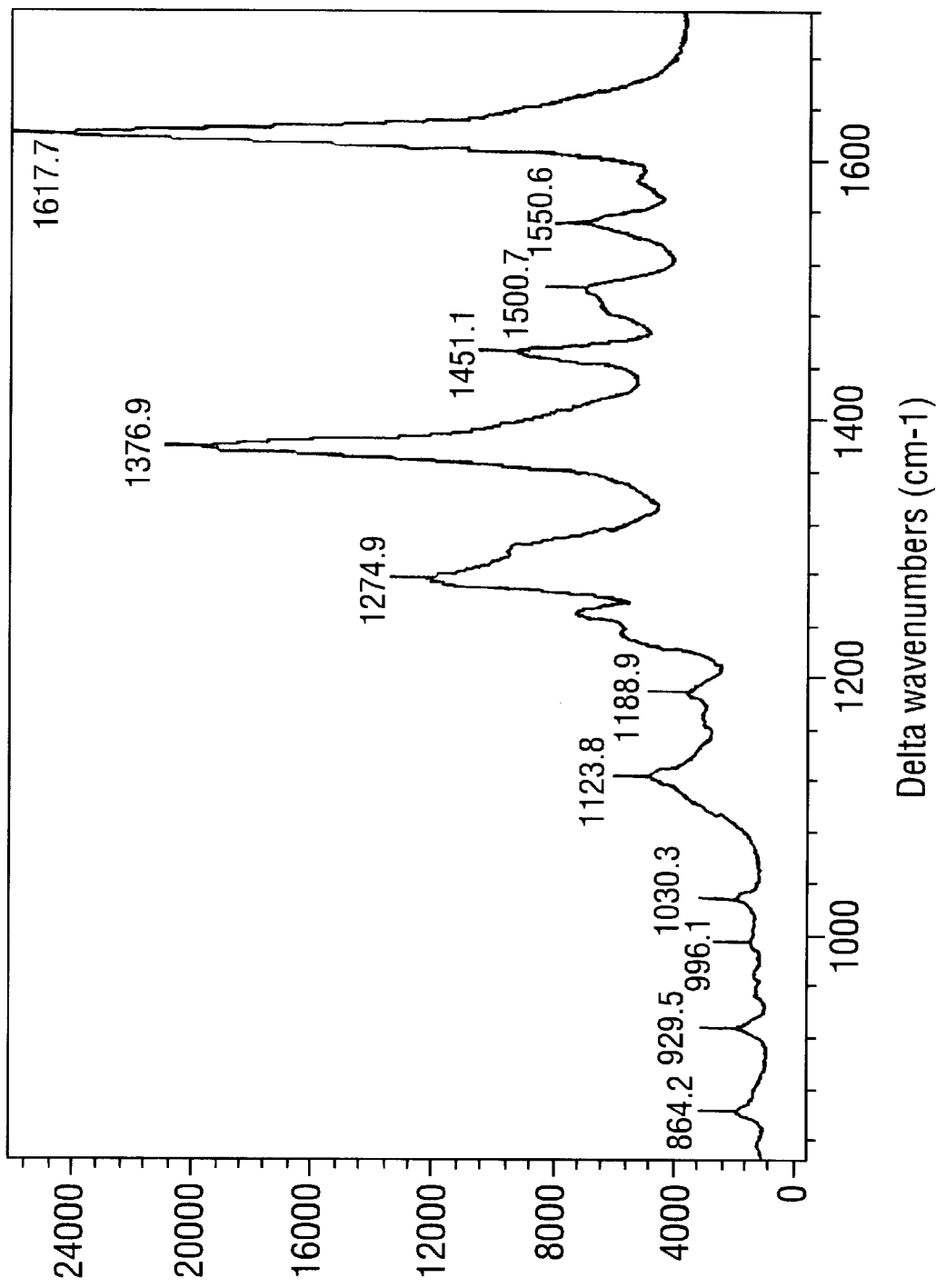

The alternative pathway shown in FIG. 2 has proved to be more successful in preparing and utilising azo dyes.

EXAMPLE 3

SERRS spectra for modified (benzotriazole) azo dyes

FIGS. 3–6 are SERRS spectra obtained for the modified azo dyes A–D respectively prepared in Example 2.

These are dyes containing the chemi-adsorptive benzotriazole group which tends to "seek out" a SER(R)S-active silver colloidal surface. Such dyes are of use as labels in the invention.

Figure 6:
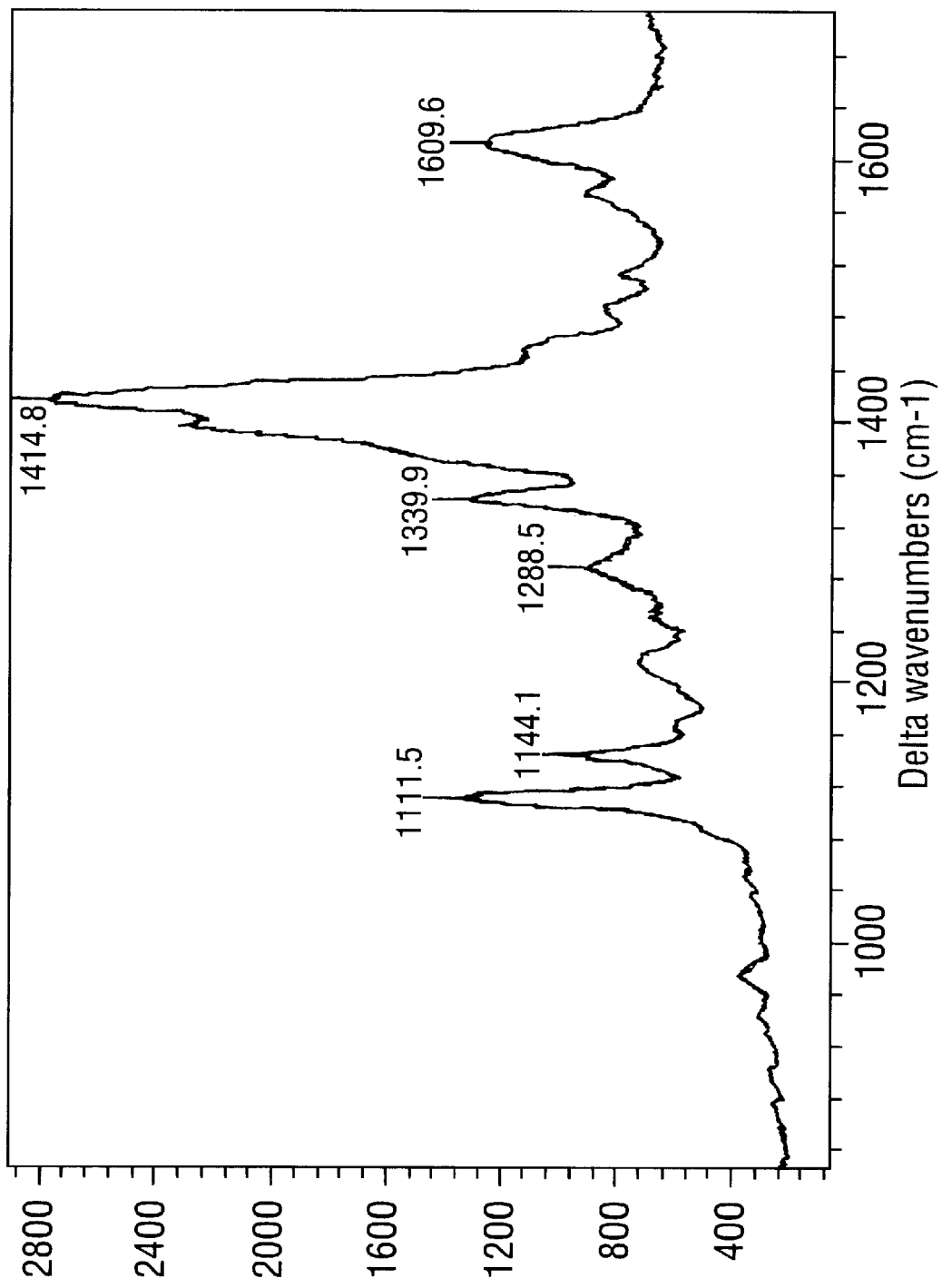

The conditions for obtaining the spectra were as follows. The SERRS-active surface was a citrate-reduced silver colloid prepared as in Example 5 below, in the form of a colloid/water mixture (1:1, 1 ml). To this was added a methanol solution of the dye in question (10 μl, approximately $10^{-5}$M) followed by spermine (20 μl, $8 \times 10^{-4}$M). Spectra were obtained using apparatus also described in Example 5. $\lambda_{max}$ for the laser was 514.5 nm; $\lambda_{max}$ values for the dyes were ~394 nm (FIG. 3), 409 nm (FIG. 4), 444 nm (FIG. 5) and 468 nm (FIG. 6).

EXAMPLE 4

Attachment of benzotriazole monoazo dyes to a nucleic acid

General method

After synthesis of the benzotriazole monoazo dye the primary amine is protected by the dimethylformamide group thus allowing selective protection of the benzotriazole secondary amine by the monomethoxytrityl group. After removal of the formamide group by treatment with base, the free amine is coupled with succinic anhydride to produce the carboxylic acid. The acid is then coupled with a methylene linker bearing a primary amine and a protected alcohol. After selective removal of the protecting group, the alcohol is phosphitylated thus producing a monomer capable of undergoing routing solid phase synthesis.

Alternatively the acid produced in the above scheme may be converted into a suitable active ester (N-hydroxysuccinimide, pentafluorophenol) and coupled with a nucleophilic primary amine at the 5'-terminus of a nucleic acid. (See J Goodchild, supra.)

Specific example

The benzotriazole monoazo dyes previously mentioned can act as the starting material for this proposed method of attachment.

Step 1

The dye (1 eq) is dissolved in anhydrous pyridine and coevaporated in anhydrous pyridine before dissolving in pyridine and dimethylformamidine dimethyl acetal (3 eq) added with stirring. After stirring at 40° C. for 2 hours the solvent is removed and the residue dissolved in ethyl acetate. After washing with saturated KCl (x3) and drying with $Na_2SO_4$, the product is purified by wet flash column chromatography eluting with methanol in dichloromethane.

Step 2

The product from step 1 (1 eq) is coevaporated with anhydrous pyridine (x3) before dissolving in anhydrous pyridine and adding dimethylaminopyridine (0.1 eq). Monomethoxytrityl chloride (1.2 eq) is added portion-wise over two hours and the mixture left to stir for four hours before methanol is added and the solvent removed in vacuo. The residue is dissolved methanolic ammonia and left to stir for 16 hours. After removal of the solvent the residue is dissolved in ethyl acetate, washed with saturated KCl (x3) and dried with $Na_2SO_4$. The product is purified by wet flash column chromatography (silica pre-equilibrated with 1% triethylamine) eluting with methanol in dichloromethane.

Step 3

The product from step 2 (1 eq) is coevaporated from anhydrous pyridine (x3) before dissolving in anhydrous pyridine and succinic anhydride (1/2 eq) added slowly. After stirring for 2 hours methanol is added and the solvent removed in vacuo. The residue is dissolved in ethyl acetate, washed with saturated KCl (x3) and dried with $Na_2SO_4$. The product is purified by either wet flash column chromatography (silica pre-equilibrated with 1% triethylamine) eluting with methanol in dichloromethane or recrystallisation from a suitable solvent.

Step 4

Aminohexanol (1 eq) is dissolved in anhydrous pyridine and dimethylaminopyridine (0.1 eq) added with stirring.

Tert-butyldiphenylsilyl chloride (1.2 eq) is added slowly and the mixture left to stir for 16 hours after which methanol is added and the solvent removed in vacuo. The residue is dissolved in ethyl acetate, washed with saturated KCl (x3) and dried with $Na_2SO_4$. The product is purified by wet flash column chromatography (silica pre-equilibrated with 1% triethylamine) eluting with methanol in dichloromethane.

Step 5

The compound produced in step 3 (1 eq) is dissolved in anhydrous dichloromethane and triethylamine (3 eq) added. The compound from step 4 (1 eq) is also added with TOPPipU (2-(2-oxo-1(2H)-pyridyl)-1,1,3,3-bidpentamethyleneuronium tetrafluoroborate) (1.1 eq) and the mixture left to stir for 18 hours. After removal of the solvent, the residue is treated with tetrabutylammonium fluoride (3 eq) in anhydrous tetrahydrofuran for a further 6 hours. Methanol and Dower resin (Py) (10 eq) are added and after stirring for one hour the mixture is filtered. After removal of the solvent the residue is dissolved in ethyl acetate, washed with saturated KCl (x3) and dried with $Na_2SO_4$. The product is purified by wet flash column chromatography (silica pre-equilibrated with 1% triethylamine) eluting with methanol in dichloromethane.

Step 6

The product from step 5 (1 eq) is coevaporated three times with anhydrous tetrahydrofuran before being dissolved in anhydrous tetrahydrofuran. Anhydrous diisopropylethylamine (4 eq) is added with stirring under argon. 2-Cyanoethyl-N,N-diisopropylchlorophosphoramidite (1.1 eq) is added dropwise and the mixture left to stir for 2 hours. Ethyl acetate is added, the organic layer washed with saturated KCl and dried with $Na_2SO_4$ and the solvent is removed in vacuo to leave an oil which is purified by wet flash column chromatography (silica pre-equilibrated with 1% triethylamine) eluting with 100% ethyl acetate.

Step 3A

The product from step 3 (1 eq) is dissolved in anhydrous dichloromethane and triethylamine (3 eq) added. Pentafluorophenol (1 eq) and TOPPipU (1.1 eq) are also added and the mixture left to stir for 18 hours. After removal of the solvent the product is purified by wet flash column chromatography (silica pre-equilibrated with 1% triethylamine) eluting with 100% ethyl acetate.

The compounds from steps 6 and 3A can then be coupled to a nucleic acid using the methods referred to previously

EXAMPLE 5

Detection of a dye-labelled modified oligonucleotide in solution

This example demonstrates a method in accordance with the invention in which spermine is used to increase sensitivity, according to feature (i), and in which a target oligonucleotide is modified according to feature (ii).

The detectability of the SER(R)S-active dye used, when attached to the modified oligonucleotide, was found to be significantly greater than was observed when the dye was attached to the same oligonucleotide sequence but with unmodified thymidine bases replacing the 5-(3-aminoprop-1-yn-1yl)-2'-deoxyuridine residues. This shows that the modifying amino groups are stabilising the interaction between the labelled DNA and the SER(R)S-active colloid surface, allowing the dye more easily to approach and reside on the surface and thereby facilitating its detection.

Method

Silver nitrate (99.9999%; Johnson Matthey), tri-sodium citrate and spermine hydrochloride (Sigma) were all of analytical grade. A 17-base DNA oligonucleotide incorporating six 5-(3-aminoprop-1-yn-1-yl)-2'-deoxyuridine residues in place of 2'-deoxythymidine was purchased from the OSWEL DNA Unit, University of Southampton. The 5'-terminus was labelled with a substituted fluorescein dye, 2,5,1',3', 7', 9'-hexachloro-5-carboxyfluorescein, available commercially as "HEX" (trade mark of P. E. Applied Biosystems) - attachment of the dye was by standard phosphoramidite chemistry (M H Caruthers, *Science* (1985), 230, pp281–285). Citrate reduced silver colloids were prepared according to the procedure of P C Lee & D Meisel, supra, modified as described below. All glassware was rigorously cleaned prior to use by treatment with aqua regia (HCl, $HNO_3$ (3+1 v/v)) followed by gently scrubbing in a soap solution and thorough rinsing with distilled water. A sample of silver nitrate (90 mg) was suspended in distilled water (500 ml, 45° C.) and heated rapidly to boiling under stirring. Immediately boiling commenced, an aqueous solution of sodium citrate (1.0%, 10 ml) was added rapidly and heating was reduced, but the solution was kept boiling gently for 90 minutes with continuous stirring, after which the final volume was adjusted to 500 ml with distilled water. For the SERRS examinations, a solution of this colloid (50% v/v) was prepared in distilled water.

A solution containing the labelled oligomer ($1\times10^{-8}$M was prepared in distilled water. An aqueous solution of spermine hydrochloride ($8\times10^{-4}$M, 20 µl) was premixed with the oligomer (20 µl) and this mixture added to an aliquot of the silver colloid solution (1 ml). An aliquot of this colloidal suspension (400 µl) was transferred to a microtitre plate for SERRS examination.

A SERRS spectrum was recorded using a 25 mW argon ion laser (514.5 nm, 1 mW) as the excitation source, using a Renishaw 2000 Spectrometer (Renishaw Ltd, Gloucestershire) and microscope. This equipment uses a cooled charge coupled device (CCD) as a detector. Ten accumulations of ten seconds each were recorded and combined to produce the final SERRS spectrum. Control spectra were obtained by examining a suspension of the above components without DNA present.

Results and Discussion

The covalently linked dye has a maximum in the absorbance spectrum at 540 nm, and a maximum in the emission spectrum at approximately 565 nm.

The surface enhanced Raman resonance scattering from the labelled oligomer was examined with excitation at 514.5 nm. Excitation at this wavelength is approximately coincident with the maximum in the absorbance spectrum and there is significant resonance enhancement from the transition which gives rise to this absorbance band.

Figure 7:
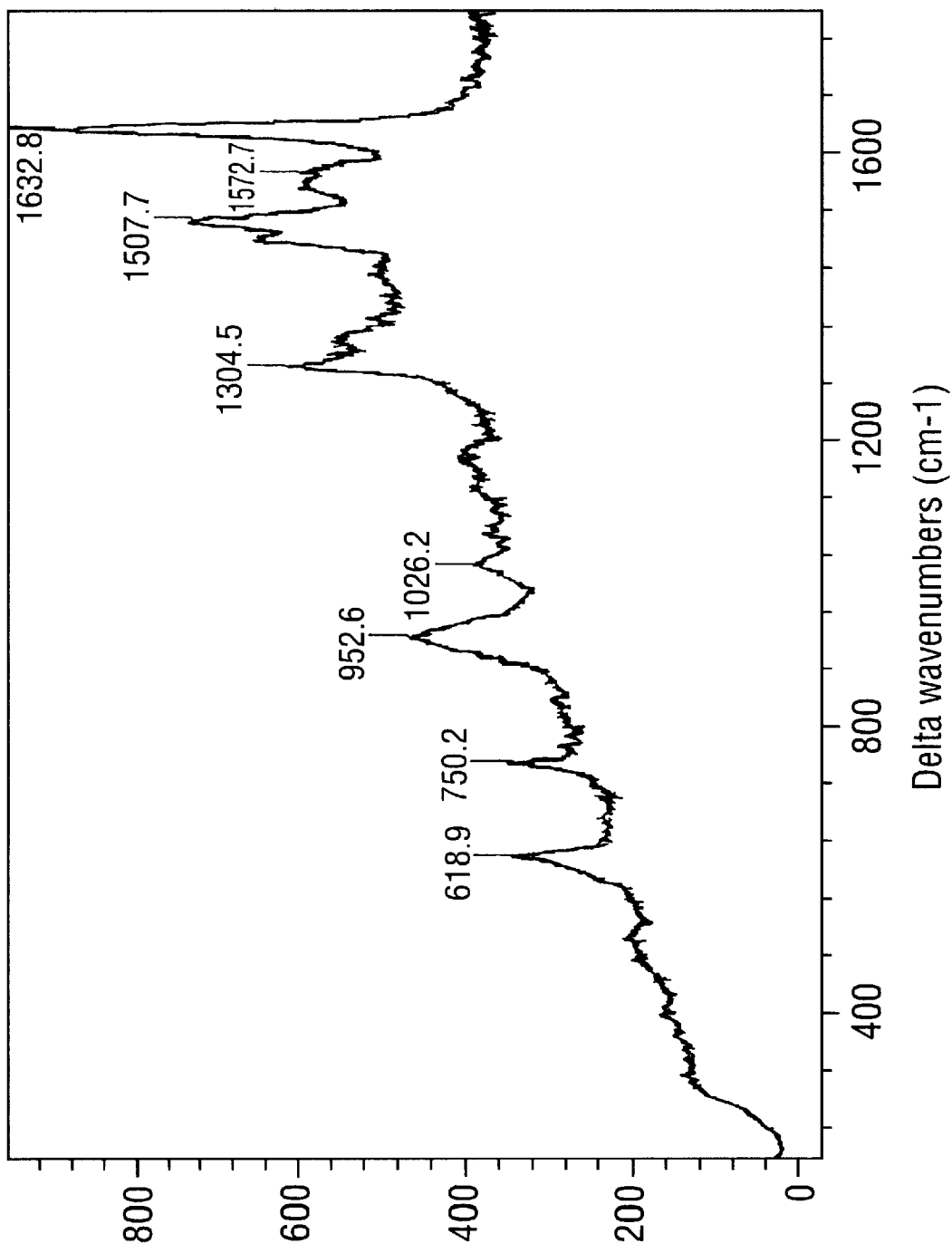
FIGS. 7 and 8 are SERRS spectra obtained by a method in accordance with the invention, for a dye labelled modified oligonucleotide in solution (Example 5)

The aliquot examined contained dye labelled oligonucleotide at a concentration of approximately $2\times10^{-10}$M, and strong SERRS signals of the order of 1000 kcounts $s^{-1}$ were observed from the dye. The spectrum is shown in FIG. 7.

Figure 8:
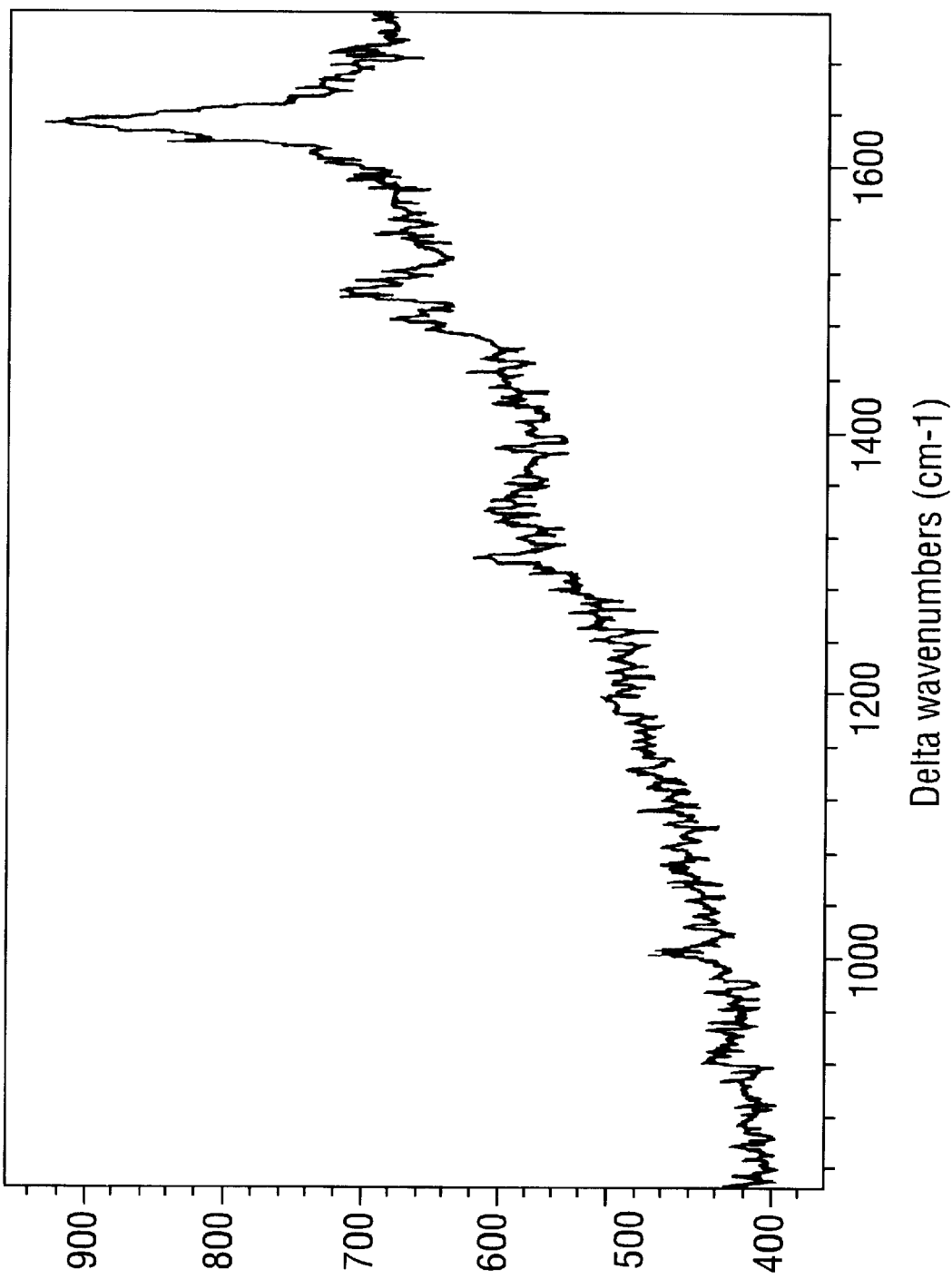

Strong SERRS signals could also be obtained from a 5 µl aliquot of the colloidal suspension added to 495 µl of distilled water—this corresponds to approximately $1\times10^{-11}$M. FIG. 8 shows the spectrum obtained.

(Comparative) EXAMPLE 6

Detection of dye labelled oligonucleotide on a nylon membrane

This experiment demonstrates the detection of an unmodified oligonucleotide in the solid phase. None of the features (i)–(iii) of the present invention was used to enhance sensitivity. The results can be compared with those of Example 7, in which features (i) and (ii) were both made use of.

Method

Citrate reduced silver colloids were prepared as described in Example 5. A HEX labelled primer containing the four common 2'-deoxynycleosides was purchased from the OSWEL DNA Unit, University of Southampton. For determination by SERRS, a solution containing the HEX labelled oligonucleotide ($1\times10^{-8}$M) was prepared in distilled water. Dilutions of this solution were prepared in distilled water to yield solutions containing the dye labelled oligonucleotide in concentrations ranging from $1\times10^{-9}$M to $1\times10^{-18}$M.

The range of concentrations ($1\times10^{-8}$ to $1\times10^{-18}$M) of the dye labelled oligonucleotide were blotted onto Hybond-N (Amersham) in $2\times1$ $\mu$l volumes. The oligonucleotide was covalently linked to the nylon membrane by irradiation at 366 nm for 45 seconds.

To obtain SERRS, poly(L-lysine) (0.01%, $2\times5$ $\mu$l) was added to the membrane and left for two minutes. Citrate reduced silver colloid ($2\times5$ $\mu$l) was then added to the membrane and the area containing the oligomer examined. SERRS was recorded using the Renishaw system described in previous examples. The time of acquisition was 5 seconds in each case.

Control spectra were obtained by examining an area of the nylon membrane which did not contain DNA, in the manner described above.

Results and Discussion

As in prior art methods, the membrane was treated with poly(L-lysine) prior to the silver colloid, rather than with a polyamine of the type preferred in the present invention.

The colloid coated membrane, mounted on an xyz stage and positioned in the laser beam using the x and y controls, was scanned until the SERRS signals were indeed from the HEX label. Control spectra of the Hybond membrane were obtained after each positive result.

Figure 9:
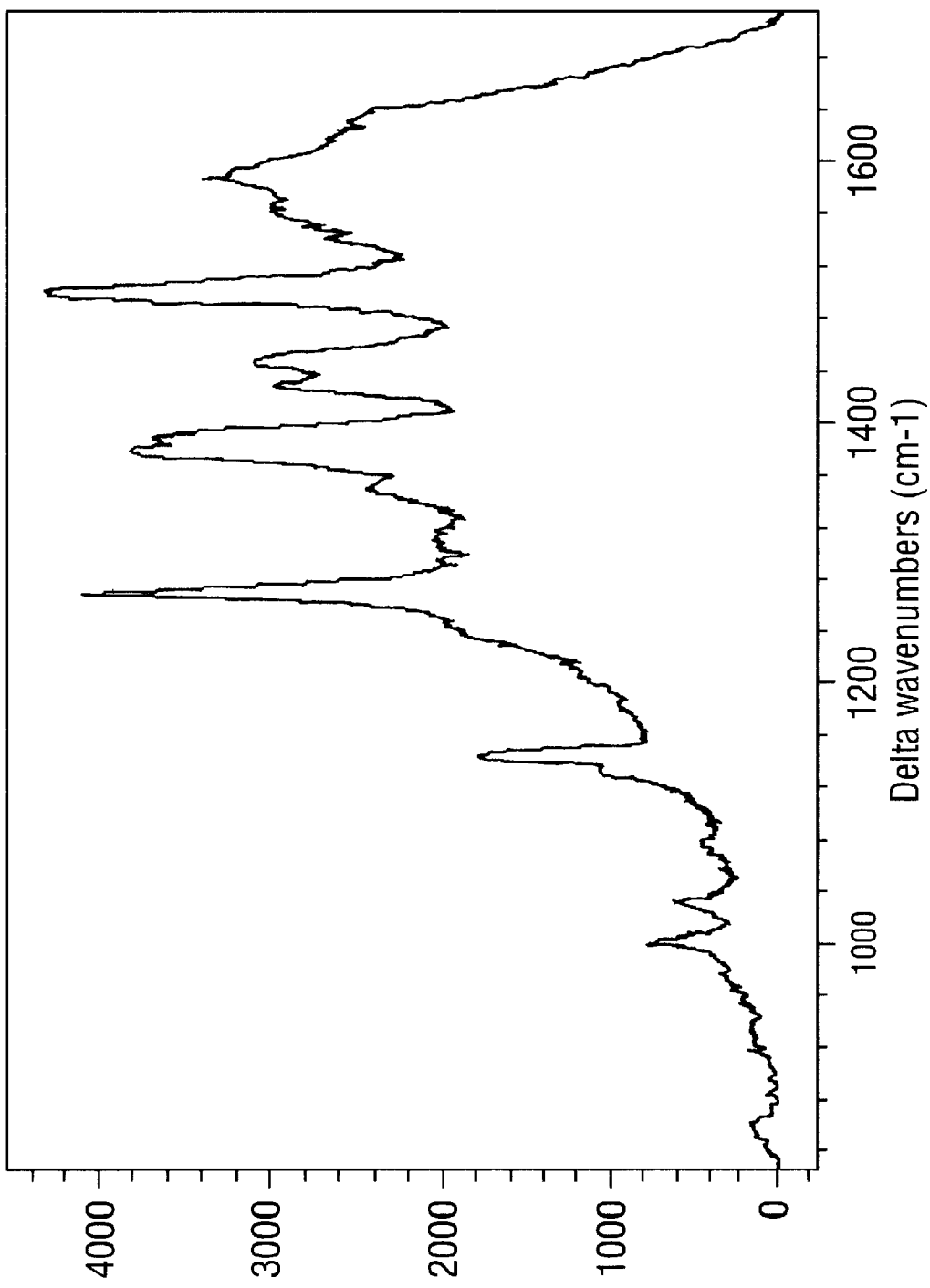
FIGS. 9–15 are SERRS spectra obtained for a dye labelled unmodified oligonucleotide on a nylon membrane (Example 6)
Figure 10:
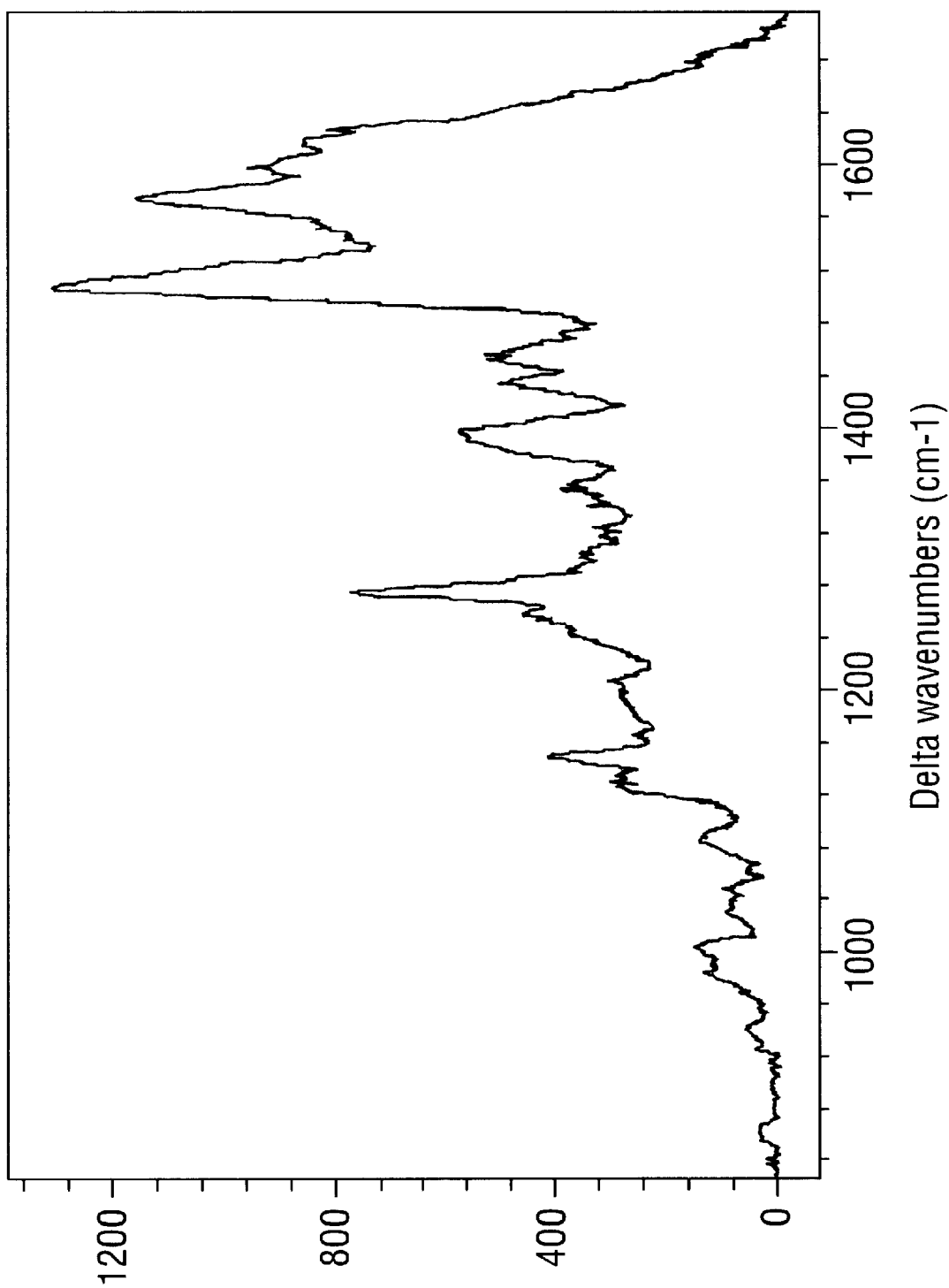
Figure 11:
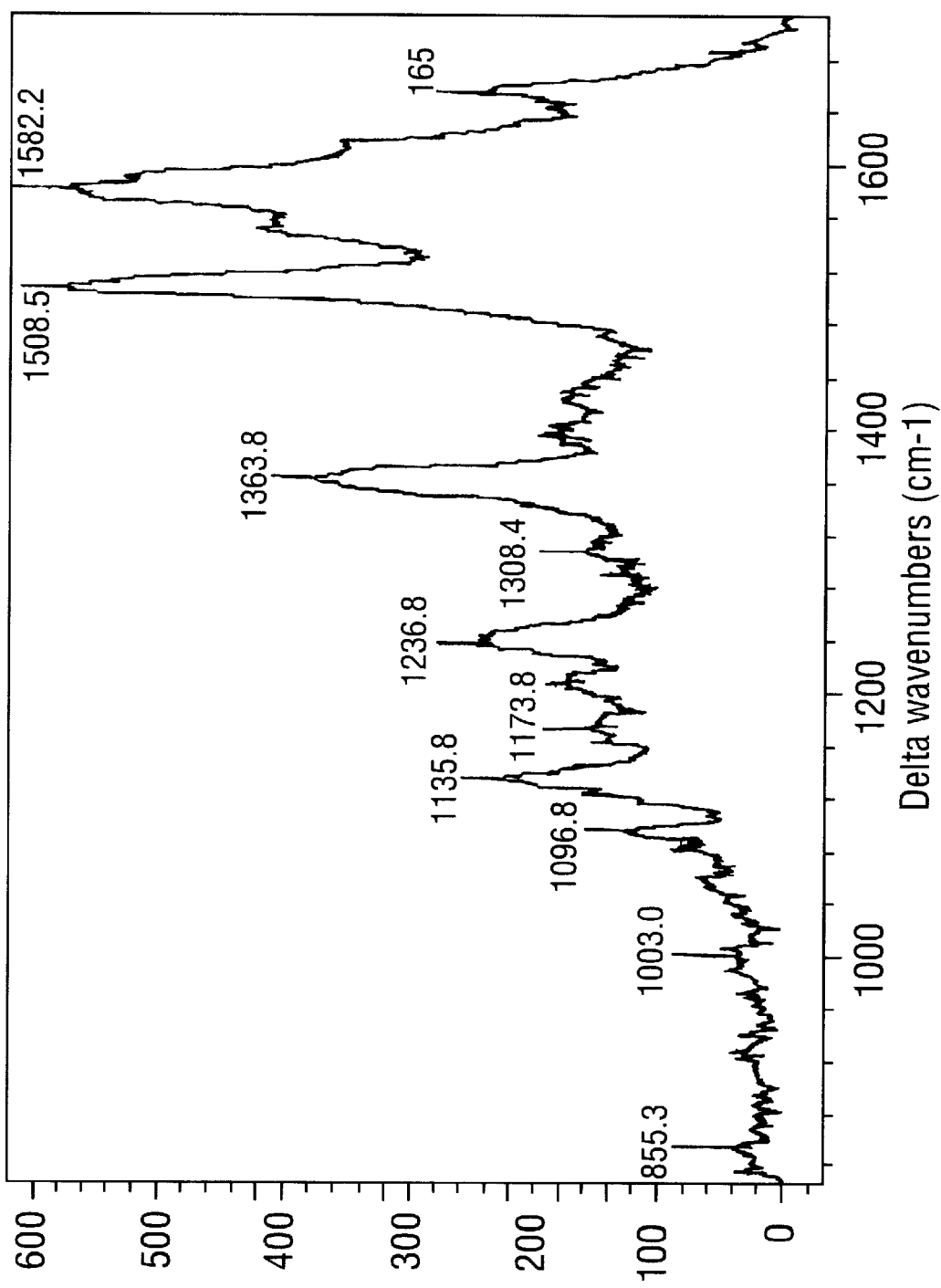
Figure 12:
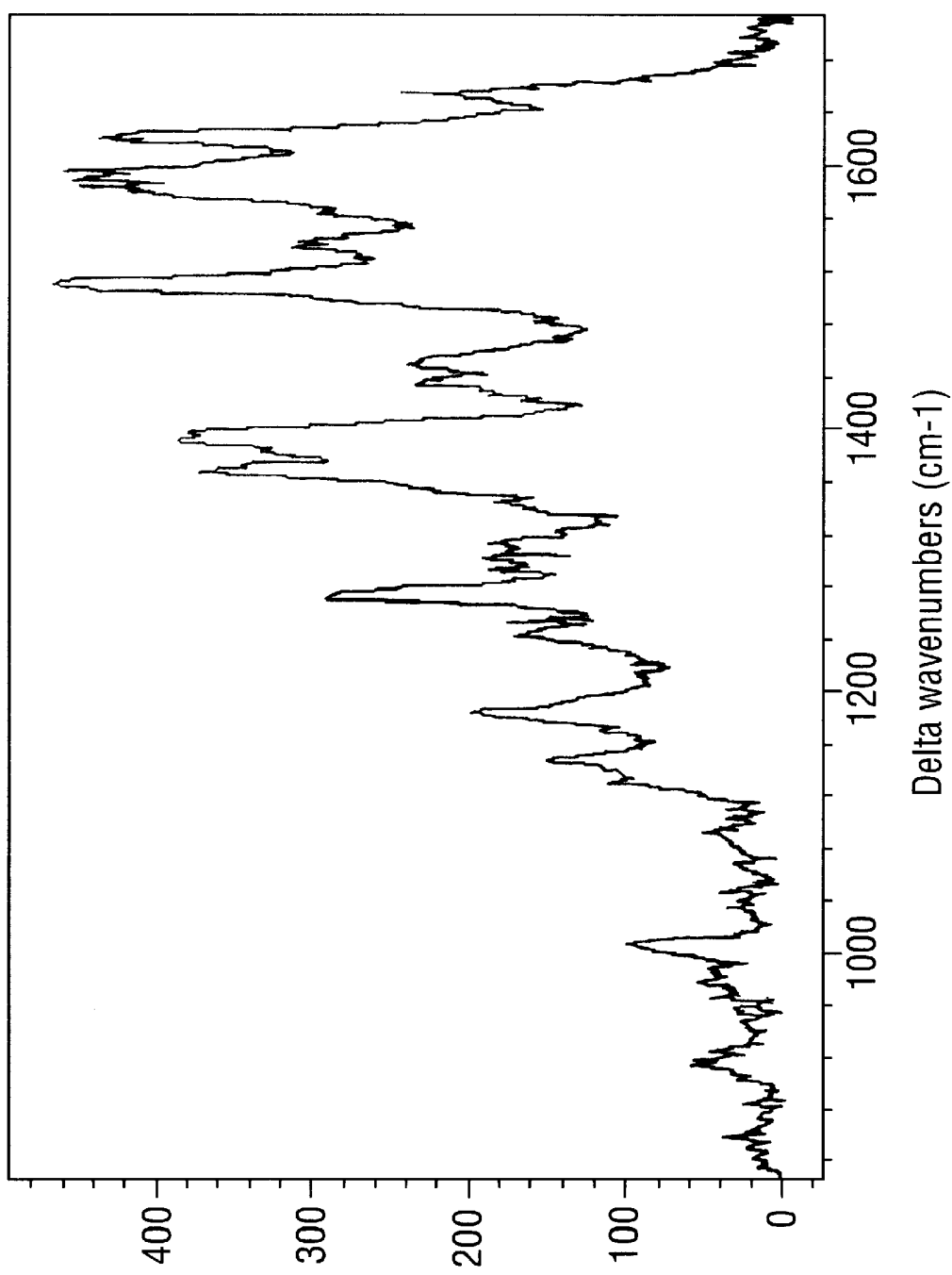
Figure 13:
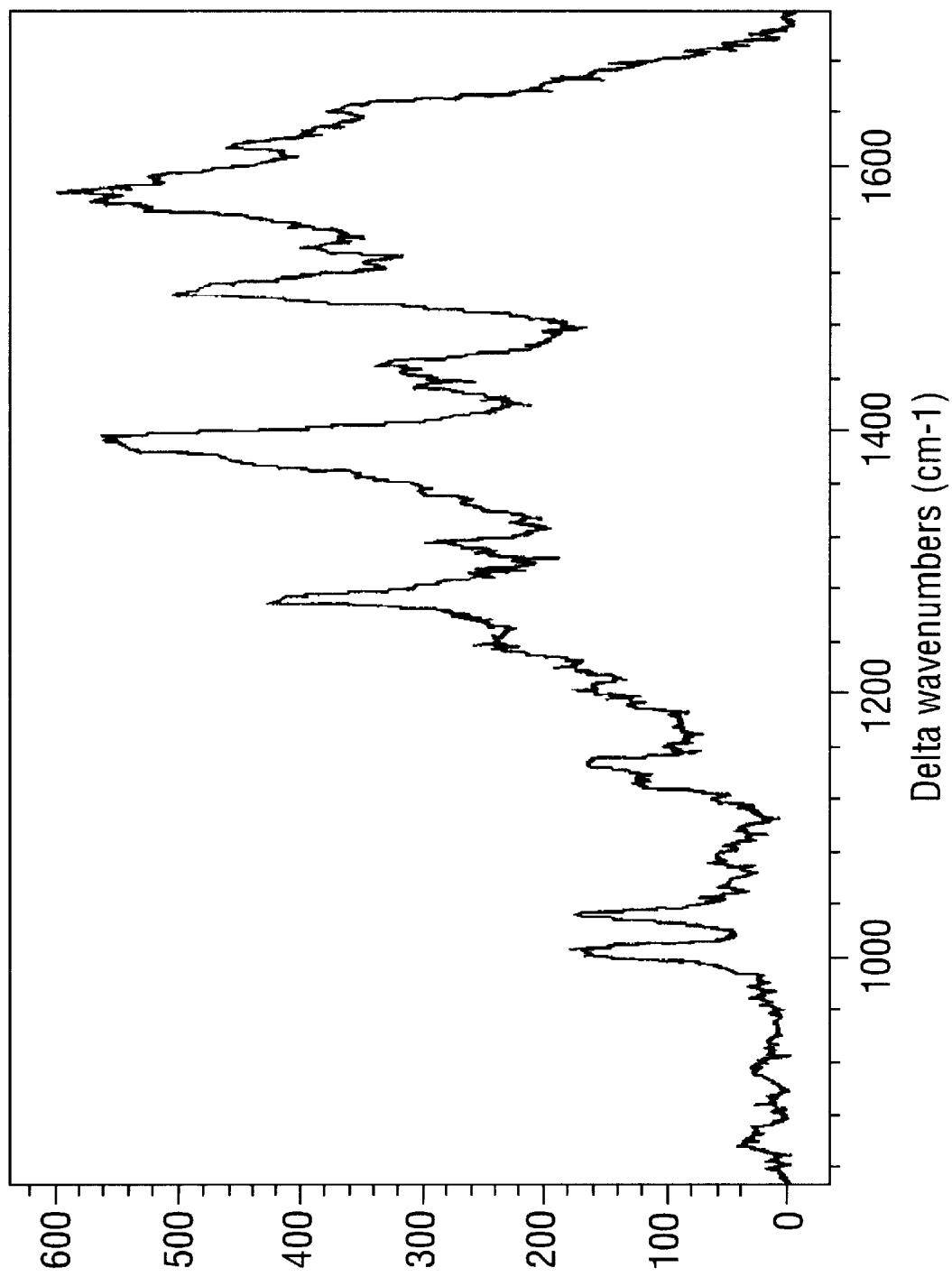
Figure 14:
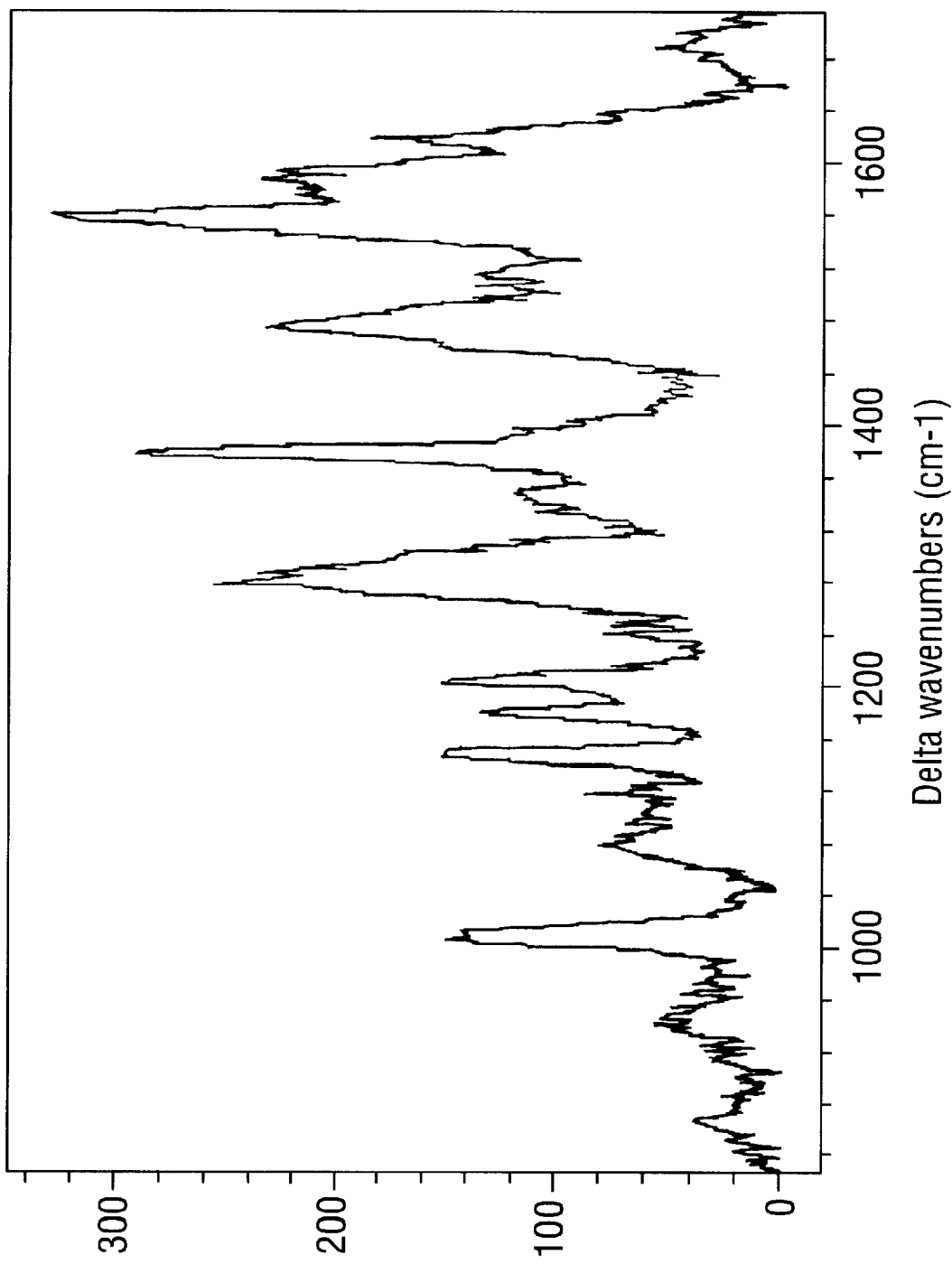
Figure 15:
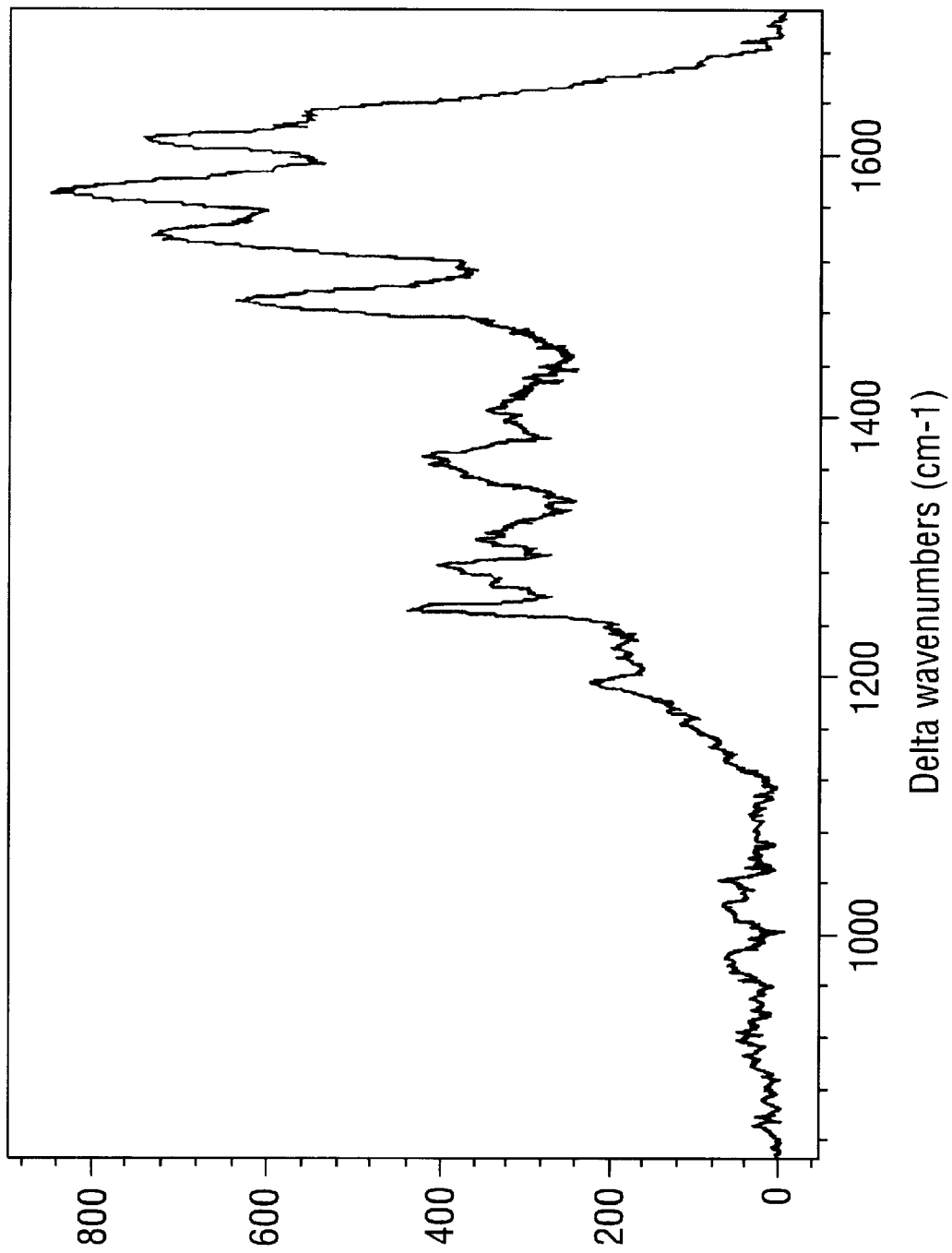

The spectra obtained are shown in FIGS. 9–15. The oligonucleotide concentrations were $1\times10^{-8}$M (FIG. 9); $1\times10^{-10}$M (FIG. 10); $1\times10^{-11}$M (FIG. 11); $1\times10^{-12}$M (FIG. 12); $1\times10^{-13}$M (FIG. 13); $1\times10^{-15}$M (FIG. 14) and $1\times10^{-16}$M (FIG. 15).

Although a positive result was obtained down to a loading concentration of $1\times10^{-16}$M, the positions of the peaks and their relative intensities appeared to differ. This is attributed to the HEX label adopting different conformations during adsorption to the surface of the silver colloid. As we are well below the concentration for monolayer coverage this result is not unexpected.

The figure of $1\times10^{-16}$M corresponds to approximately 60 molecules of labelled oligonucleotide, as only half of the oligonucleotide saturated membrane was examined in each case.

EXAMPLE 7

Detection of dye labelled modified oligonucleotide on a nylon membrane

In this experiment, the target oligonucleotide was modified to increase detection sensitivity. Spermine was also used to increase sensitivity yet further. Lower concentrations of the target were reliably detected than was possible in Example 6.

Method

Citrate reduced silver colloids were prepared as previously described. A 17-base DNA oligonucleotide containing 5-(3-aminoprop-1-yn-1yl)-2'-deoxyuridine in place of 2'-deoxythymidine was purchased from the OSWEL DNA Unit, University of Southampton and labelled at the 5'-terminus with HEX. For determination by SERRS, a solution containing the HEX labelled oligonucleotide ($1\times10^{-8}$M) was prepared in distilled water. Dilutions of this solution were prepared in distilled water to yield solutions containing the dye labelled oligonucleotide in concentrations ranging from $1\times10^{-9}$M to $11\times10^{-18}$M.

The range of concentrations ($1\times10^{-8}$ to $1\times10^{-18}$M) of the dye labelled oligonucleotide were blotted onto Hybond-N (Amersham) in $2\times1$ $\mu$l volumes. The oligonucleotide was covalently linked to the nylon membrane by irradiation at 366 nm for 45 seconds.

To obtain SERRS, spermine hydrochloride ($8\times10^{-4}$M, $2\times5$ $\mu$l) was added to the membrane. Citrate reduced silver colloid ($2\times5$ $\mu$l) was then added immediately to the membrane and the area containing the oligonucleotide examined. SERRS was recorded using the Renishaw system described in previous examples. The time of acquisition was 5 seconds in each case.

Control spectra were obtained by examining an area of the nylon membrane which did not contain DNA in the manner described above.

Results and Discussion

The membrane was treated with spermine hydrochloride prior to the silver colloid to promote the adhesion of the dye labelled oligonucleotide to the colloid surface, and the formation of stable colloidal aggregates required for a strong SERRS signal.

The colloid coated membrane, mounted on an xyz stage and positioned in the laser beam using the x and y controls, was scanned until the scattered radiation indicated a reasonable SERRS signal. To confirm the SERRS signals were indeed from the HEX label, control spectra of the Hybond membrane were obtained after each positive result.

Figure 16:
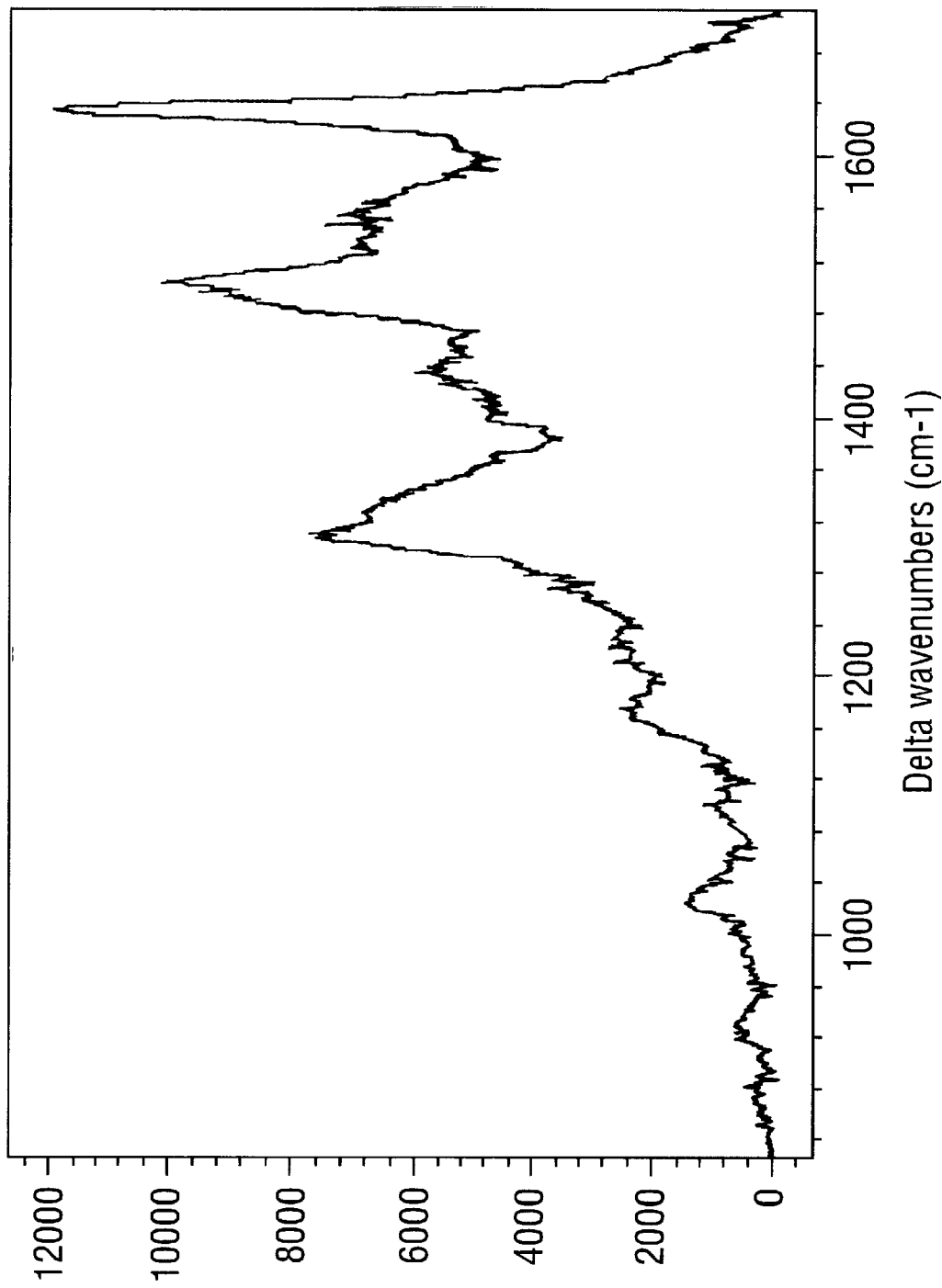
FIGS. 16–22 are SERRS spectra obtained in accordance with the invention, for a dye labelled modified oligonucleotide on a nylon membrane (Example 7).
Figure 17:
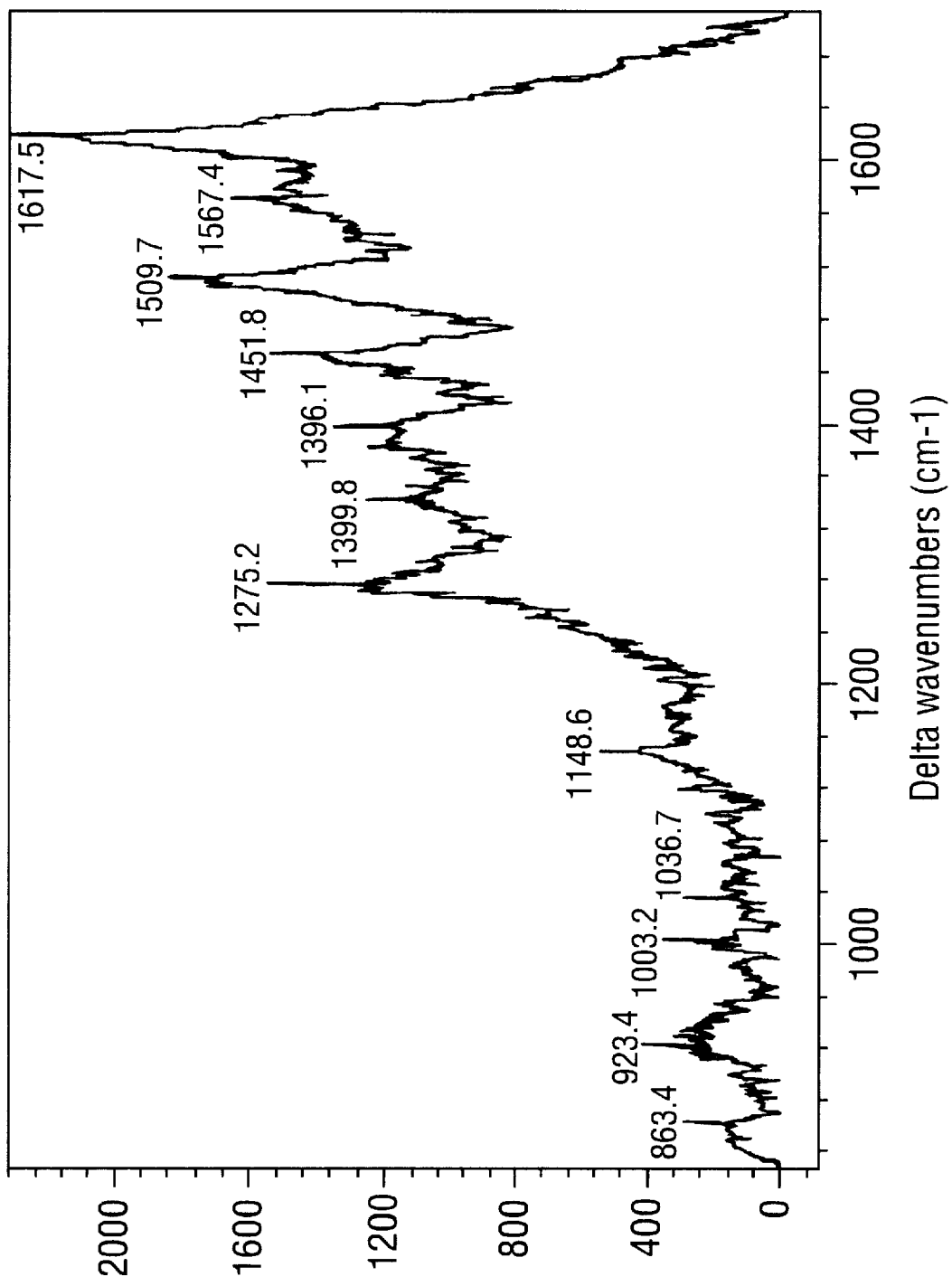
Figure 18:
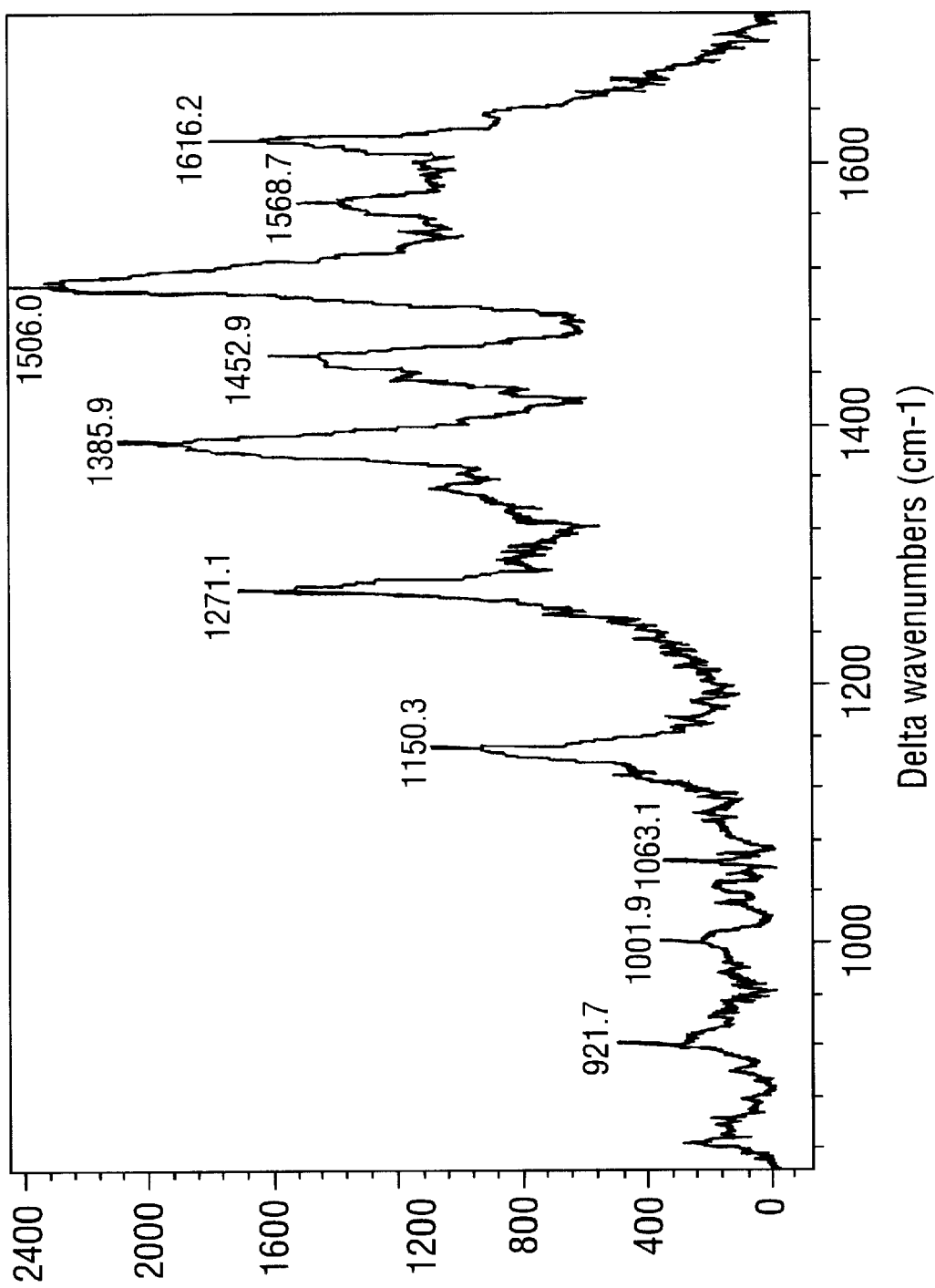
Figure 19:
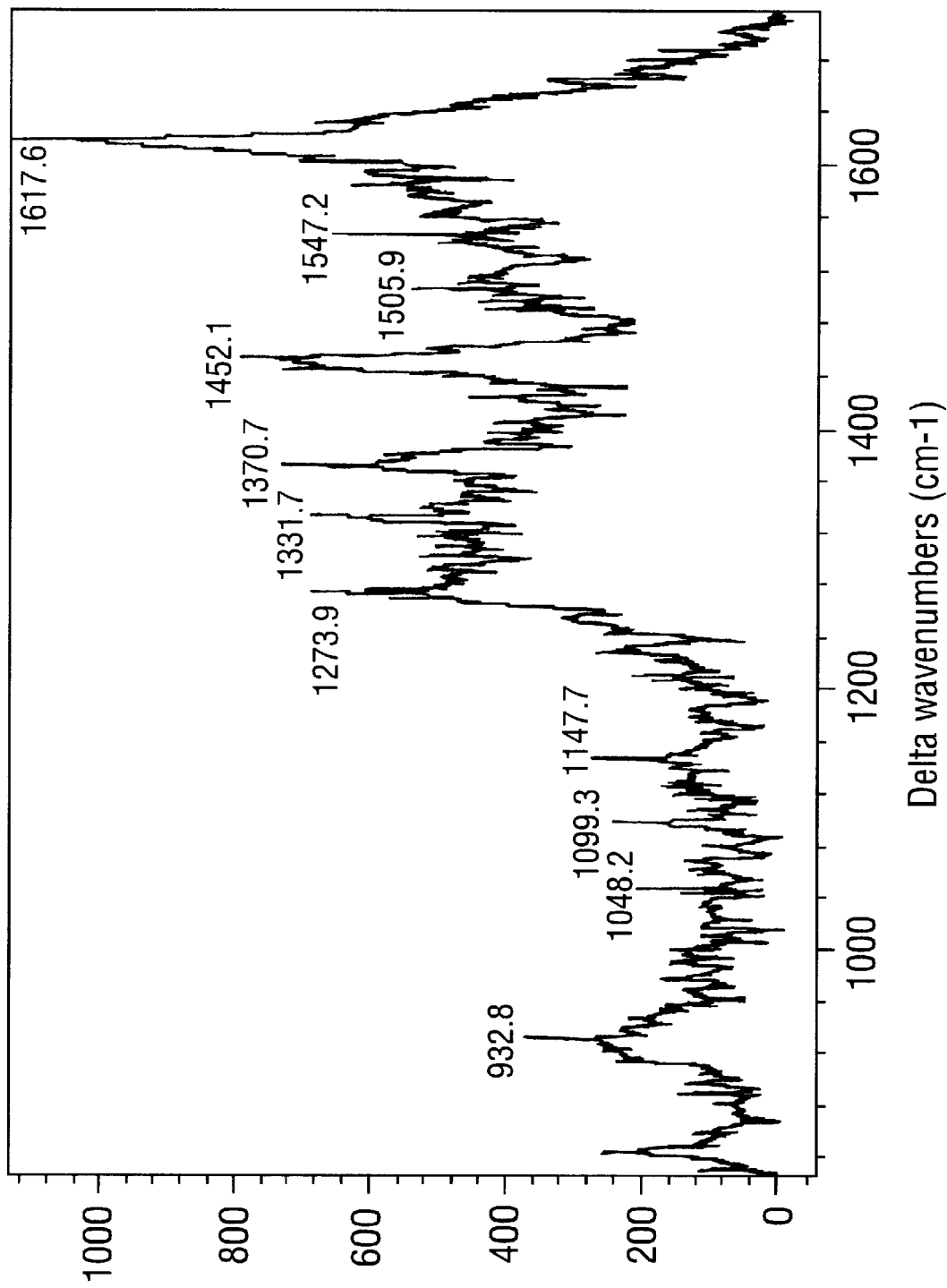
Figure 20:
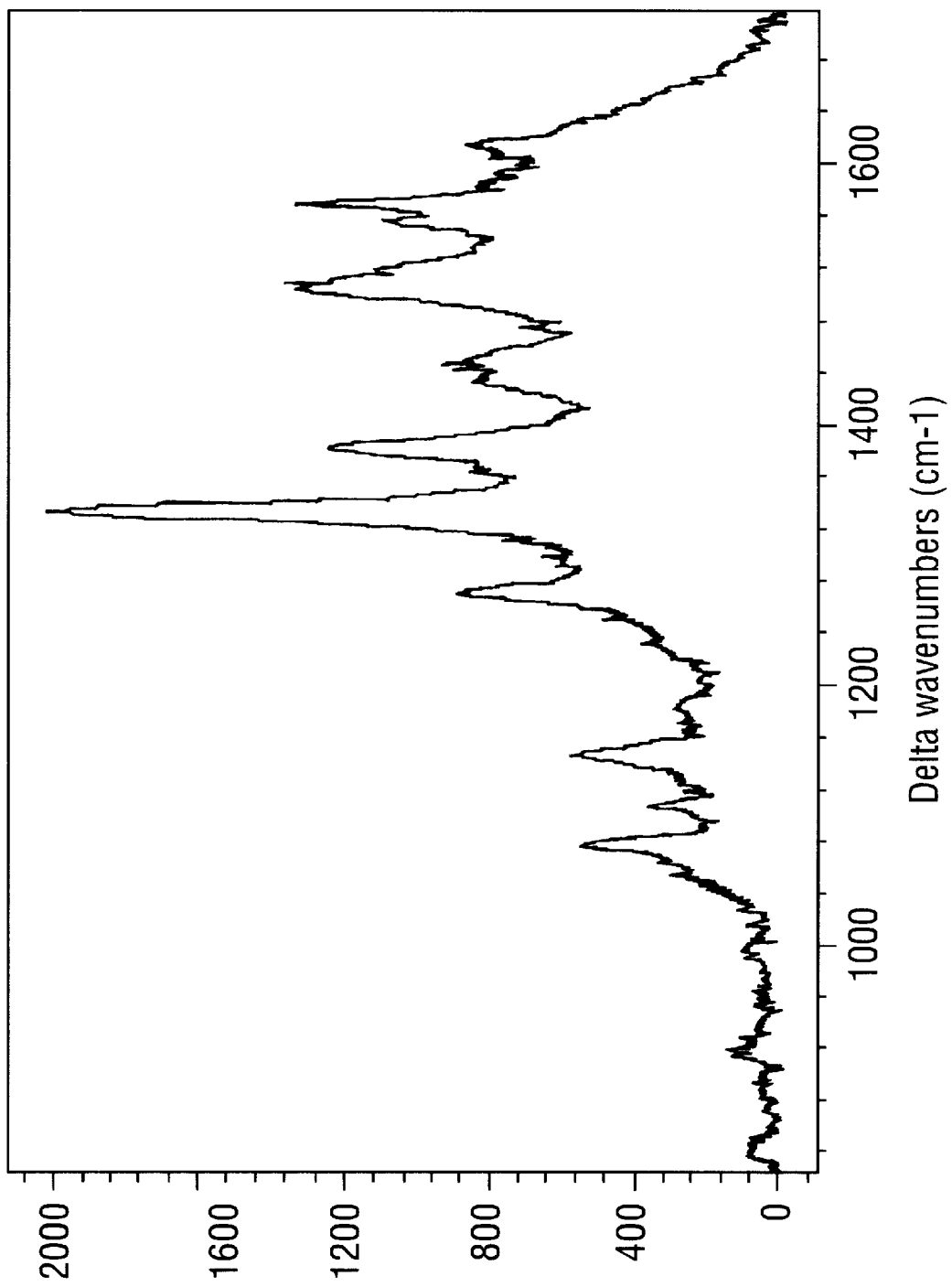
Figure 21:
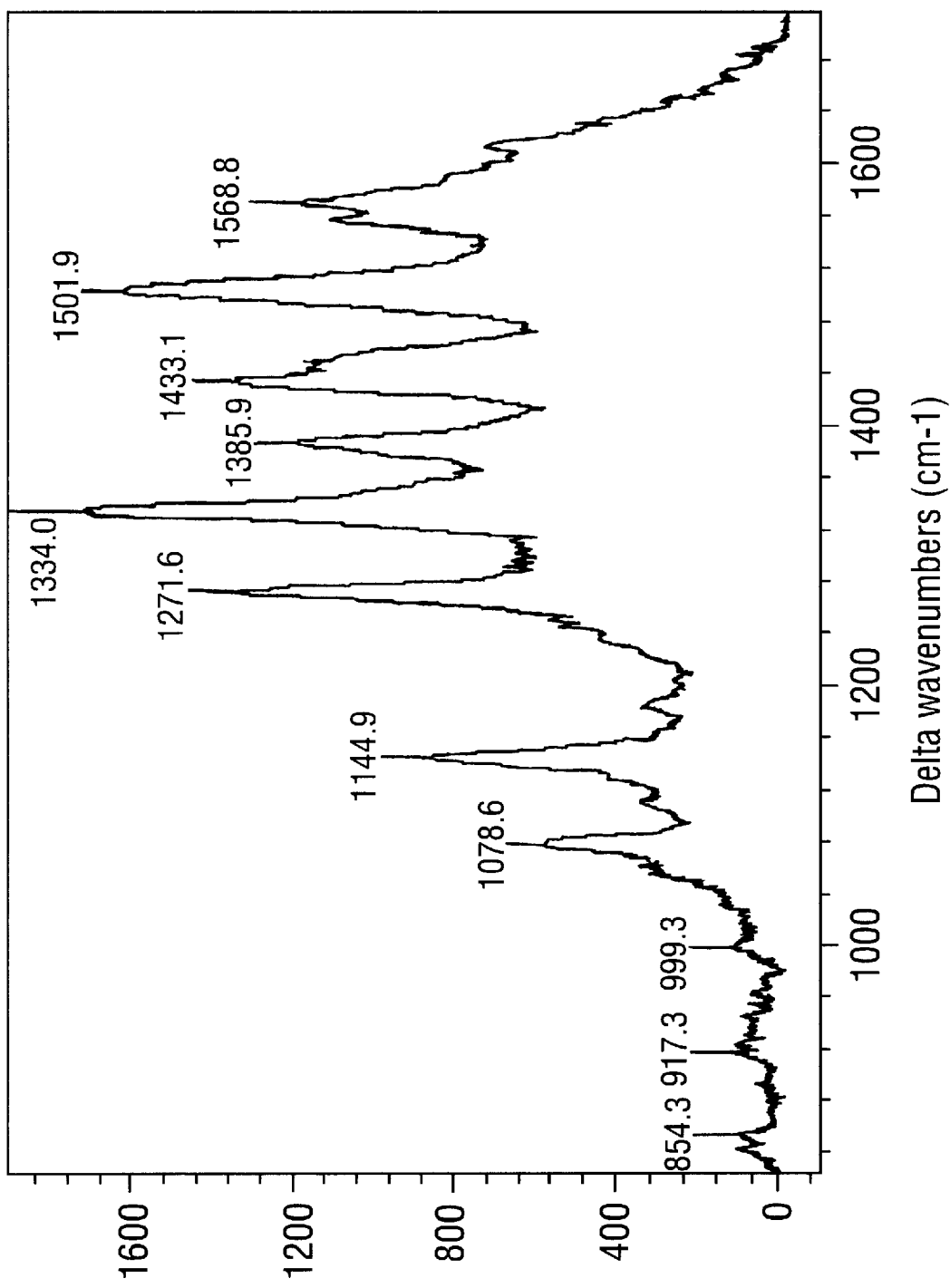
Figure 22:
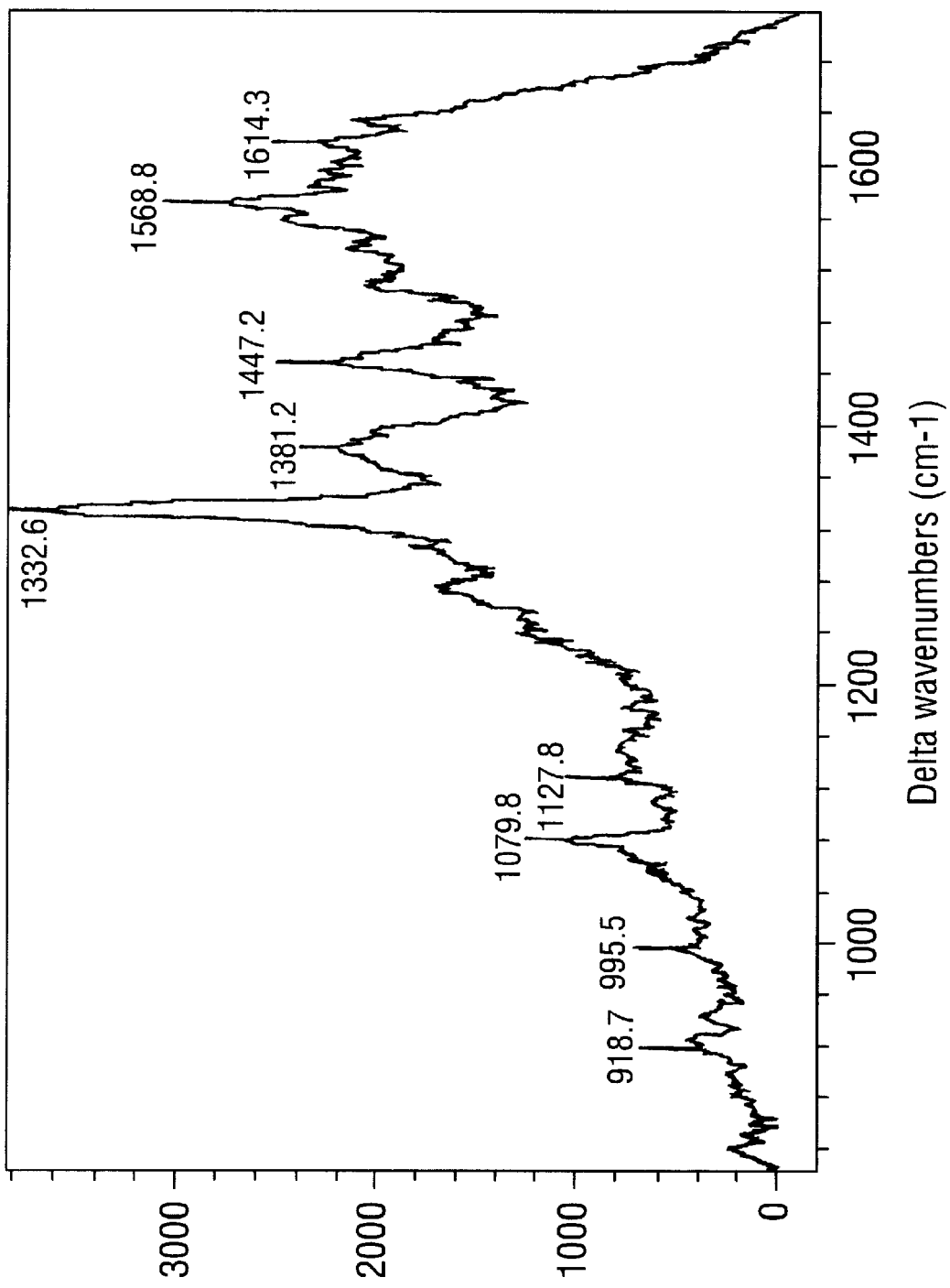

The spectra obtained are shown in FIGS. 16–22. The oligonucleotide concentrations were $1\times10^{-7}$M (FIG. 16); $1\times10^{-8}$M (FIG. 17); $1\times10^{-9}$M (FIG. 18); $1\times10^{-13}$M (FIG. 19); $1\times10^{-14}$M (FIG. 20); $1\times10^{-15}$M (FIG. 21) and $1\times10^{-17}$M (FIG. 22).

A positive result was obtained down to a concentration of $1\times10^{-17}$M, which corresponds to approximately 6 molecules of dye labelled oligonucleotide (only half of the area containing the oligonucleotide was examined in each case). The spectral quality also shows a distinct improvement over Example 6. The spectra obtained for the membrane loaded with a concentration of $1\times10^{-8}$M was identical to that obtained in Example 6, however once past this concentration the spectra changed. The relative intensities and peak positions remained the same for each spectrum from $1\times10^{-9}$M to $1\times10^{-17}$M, indicating consistent detection of the HEX label.

This method offers improved spectral quality down to a lower limit of detection than Example 6, thus facilitating analysis of very small amounts of nucleic acids accurately and with confidence.

EXAMPLE 8

Detection sensitivity for modified oligonucleotide

Based on Examples 5 and 7, the following calculations were made of the actual number of target molecules capable of being detected using the methods of the invention.

Solution phase (Example 5)

The aliquot of labelled oligomer examined contained approximately $200\times10^{-15}$ moles of the dye (HEX) labelled modified oligomer. Strong SERRS signals of the order of 1000 kcounts s$^{-1}$ were observed from the dye. Strong signals could also be obtained from a 5 $\mu$l aliquot of the colloidal suspension added to 495 $\mu$l of distilled water—this solution corresponds to approximately $10\times10^{-15}$ moles of the oligomer.

Transposing these numbers of moles into number of molecules gives rise to the following figures:

$200 \times 10^{-15}$ moles equates to $1.2 \times 10^{11}$ molecules.

$10 \times 10^{-15}$ moles equates to $6 \times 10^9$ molecules.

If the volume of the solution actually examined by the laser beam at any one time ($3.93 \times 10^{-16}$ m$^3$, 393 femtoliters) is taken into account, the following hypothetical numbers can be calculated:

$200 \times 10^{-15}$ moles equates to an average of 94.5 molecules being detected.

$10 \times 10^{-15}$ moles equates to an average of 4.7 molecules being detected.

Solid Phase (Example 7)

The spectrum obtained in the solid phase, using a concentration of $1 \times 10^{-8}$M, was identical to that obtained in the solution phase for the same concentration. After this concentration the spectrum changed to that of one with more peaks. This is thought to be due to the dye being forced to adopt a certain conformation relative to the surface of the aggregated colloid. The major difference between this study and the one conducted using poly(L-lysine) was that the subsequent spectra were almost identical in peak position and relative intensity down to a concentration of $1 \times 10^{-17}$M. This concentration corresponds to approximately six molecules in the area of study.

The spermine used in Example 7 appears to control the size of the aggregated colloid to a greater extent than does poly(L-lysine) (used in Example 6). This is suspected to give rise to greater reproducibility of spectra when using spermine.

EXAMPLE 9

Example formats for assays and sequencing techniques

The following example formats illustrate how the methods of the invention might be used in assays and sequencing techniques, in many cases improving on existing techniques. In each case, although DNA and RNA are referred to as the target nucleic acids, other nucleic acid types could be treated in the same or analogous ways.

Southern Blotting

1. Prepare DNA, restriction digest, electrophorese and blot by usual methods.
2. Hybridise with dye-labeled oligonucleotide probe (or multiple probes); probes may be charge modified with aminopropargyl or other means.
3. Wash at the optimised stringency as previously determined (wash with phosphate to minimise chloride carryover).
4. Soak with spermine.
5. Soak with reduced silver colloid.
6. Collect spectra across whole filter.
7. Use software to analyse the data and decode the mixed spectra from the various dyes.

Detection of infectious disease

1. Lyse cells with preferred method—if target is DNA, include a denaturing step.
2. Hybridise SER(R)S-active dye labelled probe(s) to target of choice (RNA or DNA).
3. Capture the hybridised material by one of a number of methods, eg, biotin capture of oligomer on the same strand as the probe target.
4. Wash away excess probe and target.
5. Add spermine, then colloid.
6. Collect spectra.
7. Species or genera may be distinguished by selection of probes and decoding the spectra of several dyes at the end. (Instead of probe hybridisation, followed by capture, a format based on extension, release and capture as for genomic variation is also possible.)

Genomic variation

1. Prepare denatured genomic target (alkaline boiling is good).
2. Hybridise dye-labelled primer with match or mismatch at the 3'-end.
3. Extend (or not, depending on the 3' match status).
4. Release newly extended material by heat or alkali denaturation or strand displacement.
5. Capture released strand using immobilised or immobilisable oligomer.
6. Wash to remove excess, unincorporated primer (may not be necessary if evanescent wave detection is done at the capture surface).
7. Develop SER(R)S effect with spermine and colloid.
8. Collect spectra as usual.

Sequencing

Format A

1. Prepare template (or genome).
2. Hybridise sequencing primer (4 parallel tubes each with a different dye attached to the primer).
3. Perform chain termination reactions with a polymerase, dNTPs and ddNTPs (a different ddNTP for each tube).
4. Pool all four reactions and resolve on a gel.
5. Transfer to membrane —blotting or elution onto moving membrane.
6. Soak with spermine and colloid.
7. Collect SER(R)S spectra and re-assemble sequence.

Format B

1. Prepare template (or genome).
2. Anneal unlabelled primer.
3. Perform chain termination reactions with polymerase, dNTP and dye-labelled ddNTPs.
4. Resolve products on sequencing gel; transfer and develop as above.

Format C

1. Perform chain termination sequencing reactions with no label on the primer or the ddNTPs (one tube per terminator base).
2. Resolve the products on polyacrylamide gel (4 wells per template); transfer to membrane by the methods as above.
3. Use a dye labelled oligomer complementary to an internal portion of the extended product, preferably very close to the primer itself, to probe the membrane.
4. After hybridisation and washing, develop the SERRS signal with spermine, colloid and spectroscopy.

In addition to the above methods in which the sequencing products are transferred to membranes, it is possible to detect SER(R)S-dye labelled material directly in the gel if one or other of the gel plates consists of a roughened SER(R)S-active surface. However, there are several issues unresolved with this; the surface may not be entirely suitable for optimally sensitive detection; no spermine is used to neutralise the net charge on the nucleic acid; and only a small proportion of the labelled target molecules can be adjacent to the silver surface.

A variation on format A makes use of multiplexing to improve throughput. A range of dye-labelled primers would be used to sequence different genomic regions. So, at step 2, each tube could have 2 or more (up to 5 or 10) differently labelled primers designed to sequence different regions. Having run four separate reactions each with up to 10 different dyes (40 days in total), the contents of the 4 tubes would be pooled, resolved and decoded as above. Because of the enormous flexibility of SER(R)S spectroscopy and the vast array of available dyes with distinguishable spectra, 40 suitable chromophores should be obtainable and the decoding of the resultant signals, although complex, should also be achievable.

By taking advantage of this multiplexing, the throughput of a sequencing project can be greatly enhanced. There is no reason to limit the targets of the sequencing reactions to one specific region; they can be broadly scattered provided there is a way to prepare sufficient usable template.

What is claimed is:

1. A method for detecting the presence of a target nucleic acid or nucleic acid unit in a sample, the method comprising the steps of:
   a) forming a primary complex between a SER(R)S-active label and any target present in the sample, optionally via a target binding species containing a nucleic acid or nucleic acid unit;
   b) preparing a detection sample in which the primary complex, or a secondary complex containing the label and the target binding species and derived directly from the primary complex, is associated with a SER(R)S-active surface; and
   c) detecting the presence of the primary or the secondary complex in the detection sample, as an indication of the presence of the target in the original sample by obtaining and analysing a SER(R)S spectrum for the detection sample;

wherein, in the detection sample, the concentration of the target present in the primary complex, or of the nucleic acid or unit contained in the target biding species in the secondary complex, is no higher than $10^{-10}$ moles per liter.

2. A method for detecting the presence or absence of a target nucleic acid or nucleic acid unit in a sample, the method comprising the steps of:
   a) forming a primary complex between a SER(R)S-active label and any target present in the sample, optionally via a target binding species containing a nucleic acid or nucleic acid unit;
   b) preparing a detection sample in which the primary complex, or a secondary complex containing the label and the target binding species and derived directly from the primary complex, is associated with a SER(R)S-active surface; and
   c) detecting the presence or absence of the primary or the secondary complex in the detection sample (and hence of the target in the original sample) by obtaining and analysing a SER(R)S spectrum for the detection sample;

wherein, at least one of the following additional steps is used:
   i) the introduction into the detection sample, prior to detection, of a monomeric or polymeric polyamine;
   ii) modification, prior to detection, of the target, and/or of the nucleic acid or nucleic acid unit contained in the target binding species, in a manner that promotes or facilitates its chemi-sorption onto the SER(R)S-active surface;
   iii) inclusion of a chemi-sorptive functional group in the SER(R)S-active label.

3. A method according to claim 2, wherein, in the detection sample, the concentration of the target present in the primary complex, or of the nucleic acid or unit contained in the target binding species in the secondary complex, is no higher than $10^{-10}$ moles per liter.

4. A method according to claim 2, wherein at least additional step (i) is used.

5. A method according to claim 4, wherein additional steps (i) and (ii) are used together.

6. A method according to claim 1, in which the presence or absence of the primary or secondary complex in the detection sample is detected by obtaining and analysing a SERRS spectrum for the detection sample.

7. A method according to claim 1, in which the target is a naturally occurring DNA or RNA or DNA or RNA unit.

8. A method according to claim 1, wherein the SER(R)S-active surface comprises an aggregation of silver colloid particles.

9. A method according to claim 2, wherein additional step (i) is used and the polyamine is a short-chain aliphatic polyamine.

10. A method according to claim 9, wherein the polyamine is spermine.

11. A method according to claim 2, wherein additional step (ii) is used and the modification of the target or target binding species facilitates its chemi-sorption onto the SER(R)S-active surface by at least partially reducing the overall negative charge of the nucleic acid or nucleic acid unit.

12. A method according to claim 11, wherein modification of the target or target binding species is achieved by incorporating into the nucleic acid or nucleic acid unit one or more functional groups comprising a Lewis base.

13. A method according to claim 12, wherein one or more amino groups are incorporated into the nucleic acid or nucleic acid unit.

14. A method according to claim 13, wherein modification of the target or target binding species is achieved by converting it into a neutral analogue.

15. A method according to claim 14, wherein the neutral analogue has one or more phosphoramide internucleotide linkages.

16. A method according to claim 2, wherein feature (iii) is used and the chemi-sorptive functional group is also a Lewis base.

17. A method according to claim 16, wherein the functional group comprises a triazole group.

18. A method according to claim 17, wherein the functional group comprises a benzotriazole group.

19. A method according to claim 18, wherein the label is an azobenzotriazole.

20. A SER(R)S-active complex comprising a target nucleic acid or nucleic acid unit bound to a SER(R)S-active label, optionally via a target binding species containing a nucleic acid or nucleic acid unit, the label being associated with a SER(R)S-active surface, and the complex being subjected to at least one of the additional steps (i)–(iii) of claim 2.

21. A SER(R)S-active complex comprising a binding species which contains a nucleic acid or nucleic acid unit and is bound to a SER(R)S-active label, the label being associated with a SER(R)S-active surface, and the complex being subjected to at least one of the additional steps (i)–(iii) of claim 2.

22. A method for sequencing a nucleic acid which comprises the use of a method according to claim 1 to detect at least one target nucleotide or sequence of nucleotides within the acid.

23. A kit for use in carrying out a method according to claim 1 or for forming a SER(R)S-active complex according to any one of claims 21–23, the kit comprising at least a SER(R)S-active label optionally bound to a binding species containing a nucleic acid or nucleic acid unit or means for preparing such a label.

24. A kit according to claim 23 additionally comprising a SER(R)S-active surface or means for preparing such a surface.

25. A kit according to claim 23, including a SER(R)S-active complex as claimed in claim 21.

26. A kit according to claim 23, additionally including a monomeric or polymeric polyamine.

27. An azobenzotriazole selected from the group consisting of:

a) 3-methoxy-4-(5'-azobenzotriazolyl)-phenylamine;

b) 3,5-dimethoxy-4-(5'-azobenzotriazolyl)-phenylamine; and c) 4-(5'-azobenzotriazolyl)-1-aminonaphthalene.

28. A method according to claim 3, wherein at least additional step (i) is used.

29. A method according to claim 28, wherein additional steps (i) and (ii) are used together.

30. A method according to claim 3, wherein additional step (i) is used and the polyamine is a short-chain aliphatic polyamine.

31. A method according to claim 30, wherein said polyamine is spermine.

32. A method according to claim 4, wherein said polyamine is a short-chain aliphatic polyamine.

33. A method according to claim 32, wherein said polyamine is spermine.

34. A method according to claim 2, in which the presence or absence of the primary or secondary complex in the detection sample is detected by obtaining and analyzing a SERRS spectrum for the detection sample.

35. A method according to claim 2, in which the target is a naturally occurring DNA or RNA or DNA or RNA unit.

36. A method according to claim 2, wherein the SER(R)S-active surface comprises an aggregation of silver colloids particles.

37. A method for sequencing a nucleic acid which comprises the use of a method according to claim 2 to detect at least one target nucleotide or sequence of nucleotides within the acid.

38. A kit for use in carrying out a method according to claim 2, the kit comprising at least one SER(R)S-active label, optionally bound to a binding species containing a nucleic acid or nucleic acid unit, or means for preparing such a label.

39. A kit for forming a SER(R)S-active complex according to claim 20, the kit comprising at least one SER(R)S-active label, optionally bound to a binding species containing a nucleic acid or nucleic acid unit, or means for preparing such a label.

40. A kit according to claim 38, additionally comprising a SER(R)S-active surface or means for preparing such a surface.

41. A kit according to claim 39, additional comprising a SER(R)S-active surface or means for preparing such a surface.

42. A kit according to claim 38, including a SER(R)S-active complex of claim 21.

43. A kit according to claim 39, including a SER(R)S-active complex of claim 21.

44. A kit according to claim 38, additionally including a monomeric or polymeric polyamine.

45. A kit according to claim 39, additional including a monomeric or polymeric polyamine.

46. A method according to claim 1, wherein said detection sample is prepared after said primary complex is formed.

47. A method according to claim 2, wherein said detection sample is prepared after said primary complex is formed.

* * * * *